United States Patent [19]

Stunnenberg et al.

[11] Patent Number: 5,017,487
[45] Date of Patent: May 21, 1991

[54] VACCINIA DNA

[75] Inventors: Hendrik G. Stunnenberg, Bammental, Fed. Rep. of Germany; Riccardo Wittek, Bussigny, Switzerland

[73] Assignee: Hoffmann-La Roche Inc., Nutley, N.J.

[21] Appl. No.: 845,014

[22] Filed: Mar. 27, 1986

[30] Foreign Application Priority Data

Apr. 4, 1985 [GB] United Kingdom ............... 8508845

[51] Int. Cl.$^5$ ...................... C12N 15/00; C12N 7/01; C12N 15/11; C12N 15/64
[52] U.S. Cl. ................................ 435/172.3; 435/235; 435/320; 435/948; 935/6; 935/32; 935/34; 935/57; 536/27
[58] Field of Search ..................... 435/68, 91, 70, 235, 435/172.3, 317, 320; 536/27; 935/32, 34, 57, 65, 12; 424/85, 89

[56] References Cited

U.S. PATENT DOCUMENTS

| | | | |
|---|---|---|---|
| 4,562,155 | 12/1985 | Ricciardi | 435/320 |
| 4,588,585 | 5/1986 | Mark | 424/985.2 |
| 4,603,112 | 7/1986 | Paoletti et al. | 435/235 |
| 4,728,609 | 3/1988 | Bhatt | 435/70 |

OTHER PUBLICATIONS

Wittek, R. et al. *J. Virol*, 49:371-378, 1984.
Sanchez-Pescador, et al. *Science*, 227:484-492, 1985.
Smith et al. (1984) Biotechniques, Nov./Dec., pp. 306-312.
Smith et al. (1984) *Science*, 224, 397-399.
Darnell et al., *Molecular Cell Biology*, Scientific American Books (New York:NY), 1986, p. 348.
Bertholet et al., Proc. Natl. Acad. Sci. USA, 82:2096-2100 (1985).
Moss et al., European Patent Application Publication No. 0110385 (1984).
Panicali et al., Proc. Natl. Acad. Sci. USA, 80:5364-5368 (1983).
Paoletti et al., Proc. Natl. Acad. Sci. USA, 81:193-197 (1984).
Hope et al., Nucleic Acids Research 13:369 (1985).
Kaplan, British Med. Bull. 25:131 (1969).
Kieny et al., Nature 312:163 (1984).
Mackett et al., J. Virol. 49:857 (1984).
Panicali et al., Proc. Natl. Acad. Sci. USA 79:4927 (1983).
Smith et al., Biotechnology and Genetic Engineering Reviews 2:383 (1984).
Weir et al., J. Virol. 46:530 (1983).
Weir et al., J. Virol. 51:662 (1984).

*Primary Examiner*—Richard A. Schwartz
*Assistant Examiner*—Johnny F. Railey, II
*Attorney, Agent, or Firm*—George M. Gould; Bernard S. Leon; William H. Epstein

[57] ABSTRACT

New transcriptional regulatory sequences useful in the expression of pro- or eukaryotic proteins in eukaryotic organisms are provided comprising the 5' flanking region of the vaccinia virus late 11 kDa gene. Also described are recombinant vectors and recombinant infectious poxviruses containing such transcriptional regulatory sequences operatively linked to foreign genes, and live vaccines based upon these recombinant infectious poxviruses.

38 Claims, 16 Drawing Sheets

F I G. 9a
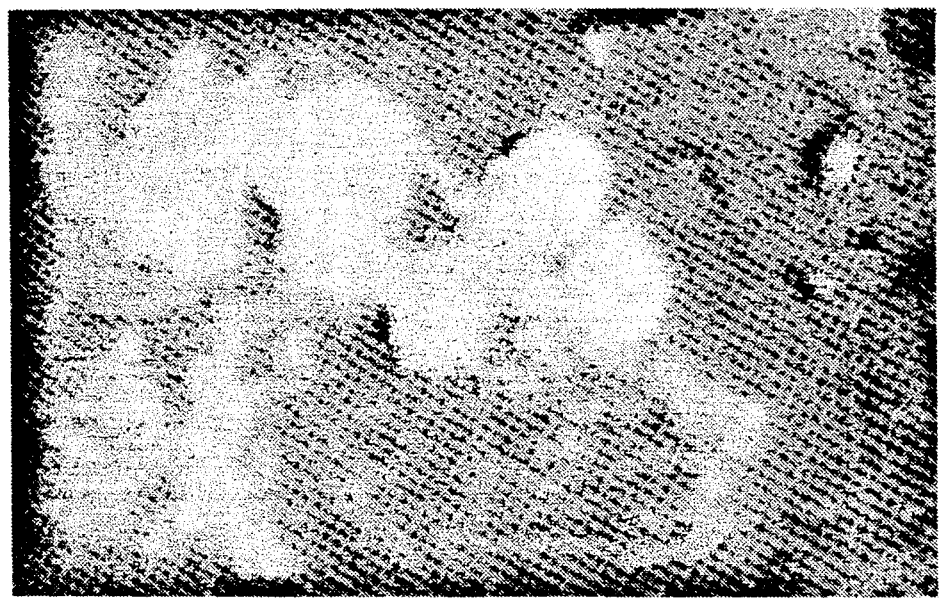
F I G. 9b

VACCINIA DNA

TECHNICAL FIELD

The present invention deals with vaccinia DNA transcriptional regulatory sequences from the 5' flanking region of the vaccinia virus late gene encoding a basic polypeptide with a molecular weight of 11,000 (11 kDa), recombinant vectors useful for the insertion of foreign genes into poxvirus, recombinant infectious poxviruses containing foreign genes operatively linked to such transcriptional regulatory sequences and capable of effecting expression of the corresponding polypeptide and live vaccines based upon such recombinant infectious poxviruses. Preferred poxviruses used in this invention are vaccinia viruses.

BACKGROUND OF THE INVENTION

Vaccinia virus is the prototype for the orthopoxvirus of the poxvirus family. Its biology and replication have been described extensively by B. Moss ("Poxviruses", in Comprehensive Virology, eds. H. Fraenkel-Conrat and R. Wagner, Plenum Press, New York, Vol. 4, pp. 405–474 [1974]; "Poxviruses", in Molecular Biology of Animal Viruses, ed. D. P. Nayak, Marcel Dekker, New York, Vol. 2, pp. 849–890 [1978]; "5' End Labelling of RNA with Capping and Methylating Enzymes", in Gene Amplification and Analysis, eds. J. G. Chirikjian and T. S. Papas, Elsevier, North-Holland, Vol. 2, pp. 254–266 [1981]; "Principles of Virus Replication: Poxvirus", in Human Viral Diseases, eds. B. N. Fields, R. Chanock, R. Shope and B. Roizman, Raven Press, New York, in press [1984]). While several types of animal DNA viruses with large enomes have been used as cloning vectors, including adenovirus, herpes simplex virus and vaccinia virus, only recombinants of the latter have expressed foreign genes while retaining complete infectivity. Meanwhile great experience has been gained with the use of vaccinia virus as a live vaccine. Its wide host range, large capacity for foreign DNA and inability to induce oncogenic transformation are all features enhancing the potential of vaccinia virus recombinants as live vaccines. AN updated review of the use of recombinant vaccinia viruses as live vaccines has been given by G. L. Smith et al. (Biotechnology and Genetic Engineering Reviews 2, 383–407, [1984]), including a description of the biology of recombinant vaccinia viruses and the expression of foreign genes under the control of vaccinia promoters.

SUMMARY OF THE INVENTION

The gene coding for a major late 11 kDa structural polypeptide of the vaccinia virus which has been mapped by R. Wittek et al. (J. Virol. 49, 371–378 [1984]) has been sequenced including its 5'-flanking region. The DNA sequence of above gene and derived amino acid sequence is indicated below:

GTACCAAATTCTTCTATCTCTTTAACTACTTGCATAGA

TAGGTAATTACAGTGATGCCTACATGCCGTTTTTTGAA

↓

ACTGAATAGATGCGTCTAGAAGCGATGCTACGCTAGT

CACAATCACCACTTTCATATTTAGAATATATGTATGTA

-continued
AAAATATAGTAGAATTTCATTTTGTTTTTTTCTATGCTA

Met Asn Ser His Phe Ala Ser Ala His Thr Pro Phe
TAAATGAATTCTCATTTTGCATCTGCTCATACTCCGTTT
↑

Tyr Ile Asn Thr Lys Glu Gly Arg Tyr Leu Val Leu
TATATCAATACCAAAGAAGGAAGATATCTGGTTCTA

Lys Ala Val Lys Val Cys Asp Val Arg Thr Val Glu
AAAGCCGTTAAAGTATGCGATGTTAGAACTGTAGAA

Cys Glu Gly Ser Lys Ala Ser Cys Val Leu Lys Val
TGCGAAGGAAGTAAAGCTTCCTGCGTACTCAAAGTA

Asp Lys Pro Ser Ser Pro Ala Cys Glu Arg Arg Pro
GATAAACCCTCATCGCCCGCGTGTGAGAGAAGACCT

Ser Ser Pro Ser Arg Cys Glu Arg Met Asn Asn Pro
TCGTCCCCGTCCAGATGCGAGAGAATGAATAACCCT

Arg Lys Gln Val Pro Phe Met Arg Thr Asp Met Leu
AGAAAACAAGTTCCGTTTATGAGGACGGACATGCTA

Gln Asn Met Phe Ala Ala Asn Arg Asp Asn Val Ala
CAAAATATGTTCGCGGCTAATCGCGACAACGTGGCG

Ser Arg Leu Leu Asn
TCGAGGCTTTTGAACTAAAATACAATTATATCCTTTTC

GATATTAATAAATCCGTGTCGTCAAGGTTTTTTATC

The 5'-flanking region shows little homology to either the corresponding region of vaccinia early genes (Weir, J. P. and B. Moss, J. Virol. 51, 662–669 [1984]) or to consensus sequences characteristic of most eukaryotic genes. Furthermore, it has been found that a DNA fragment, the 5' end of which is located within 100 base pairs from the 5'-flanking region of the 11 kDa gene (position indicated by arrows above), contains all necessary transcriptional regulatory signals for correct regulation of vaccinia virus late gene expression.

Therefore, the present invention comprises a transcriptional regulatory sequence of the following formula:

```
       100       90        80
5' CTAGA  AGCGA TGCTA  CGCTA GTCAC  AATCA 70        60        50
   CCACT  TTCAT ATTTA  GAATA TATGT  ATGTA 40        30        20
   AAAAT  ATAGT AGAAT  TTCAT TTTGT  TTTTT

10
   TCTAT  GCTAT AAATG 3'
``` or subunits (fragments) thereof which are capable of regulating expression of foreign genes.

In addition it has been found that a DNA fragment of not more than 13 contiguous bases counted from position 2 at the 3'-end of above transcriptional regulatory sequence constitutes a preferred element for correct regulation of vaccinia virus late gene expression. Therefore such 3'-end transcriptional regulatory sequences (fragments) also belong to the present invention and are encompassed by the present application.

Furthermore, the invention comprises variations of any of the foregoing transcriptional regulatory sequences including deletions, insertions, substitutions, inversions of single or several nucleotides and combinations thereof capable of functioning as a poxvirus late promoter (functionally equivalent derivatives).

Specific examples of functional variations of the above mentioned transcriptional regulatory sequences are represented by the following formulas:

5' CTAGA AGCGA TGCTA CGCTA GTCAC AATCA

CCACT TTCAT ATTTA GAATA TATGT ATGTA AAAAT

ATAGT AGAAT TTCAT TTTGT TTTTT AAAGG ATCTA

TAAAT AAAT 3' and

5' CTAGA AGCGA TGCTA CGCTA GTCAC AATCA

CCACT TTCAT ATTTA GAATA TATGT ATGTA AAAAT

ATAGT AGAAT TTCAT TTTGT TTTTT TCTAT CGATT

AAATA AAG 3'

The invention also encompasses tandem repeats, e.g. from 2 to 5 times, of the above-mentioned transcriptional regulatory sequences.

The invention further comprises recombinant vectors containing a chimeric gene comprising at least one transcriptional regulatory sequence of the vaccinia major late 11 kDa gene operatively linked to a foreign gene encoding prokaryotic or eukaryotic polypeptides, DNA from a non-essential segment of the poxvirus genome flanking said chimeric gene, the vector origin of replication and antibiotic resistence genes. As used herein the term "polypeptides" is meant to include both polypeptides and larger proteins. The translational initiation site of the chimeric gene is provided either by the transcriptional regulatory sequence of the vaccinia major 11 kDa gene or by the foreign gene encoding prokaryotic or eukaryotic polypeptides. By using the translational initiation site of the foreign gene codon, phasing and potential problems associated with biological activity of fusion proteins are avoided. Preferred recombinant vectors using the translational initiation site of the transcriptional regulatory sequence of the vaccinia major 11 kDa gene or the translational initiation site of the foreign gene are described in Examples 1-4, infra.

BRIEF DESCRIPTION OF THE FIGURES

The present invention may be more readily understood by reference to the following figures, in which symbols are used to represent the vaccinia virus TK-gene ( ⎯⎯⎯→ ), the transcriptional regulatory sequences of the 11 kDa protein of vaccinia virus ( ▭▭▭▷ ), the gene for the 5.1 antigen of *Plasmodium falciparum* ( ▬▬▬ ) and the gene for mouse dihydrofolate reductase ( ▦▦▦▦▷ ), and wherein FIG. 1 Part (a) is a schematic outline of the construction of plasmid pBR-J comprising pBR-322 and the HindIII "J" fragment of vaccinia virus, containing the vaccinia virus TK-gene. Part (b) is a schematic outline of the construction of plasmid pBR-F1 comprising pBR-322 and the righthand side of the HindIII-F fragment of vaccinia virus, containing the transcriptional regulatory sequences of the 11 kDa protein of vaccinia virus;

FIG. 9 represents indirect immunofluorescence of cells infected with the virus RVV-4 containing the *Plasmodium falciparum* 5.1 antigen. Panel A cells were photographed under 450-490 nm illumination, while panel B cells were photographed with ordinary light phase contrast;

DESCRIPTION OF THE INVENTION

Figure 1A:
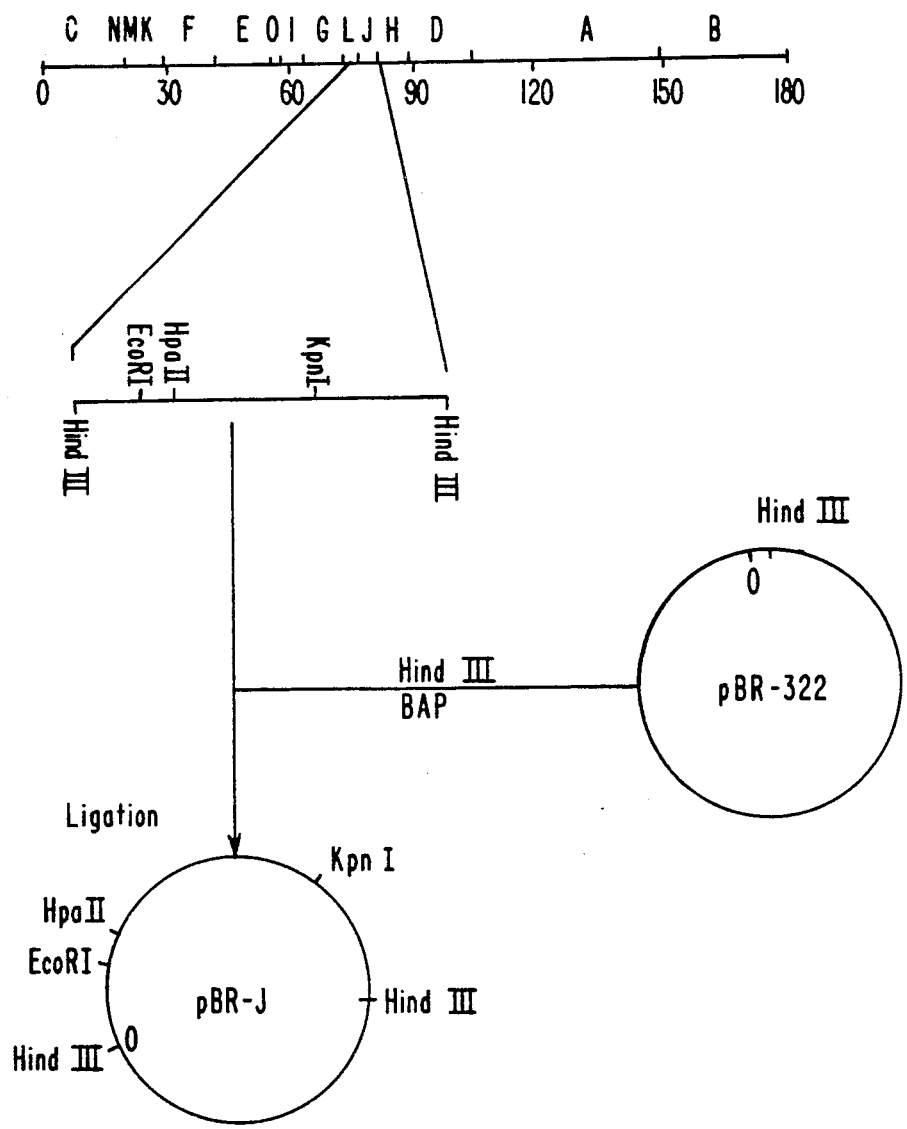

The recombinant vectors of this invention can be constructed by methods well known in the art (D. Panicali and E. Paoletti, Proc. Natl. Acad. Sci. U.S.A. 79, 4927–4931 [1983]; D. Panicali et al., Proc. Natl. Acad. Sci. U.S.A. 80, 5364–5368 [1984]; G. L. Smith et al., supra; M. Mackett et al., J. Virol. 49, 857–864 [1984]) comprising the steps of:

(a) preparing a vector containing poxvirus DNA, said DNA comprising:
  (i) at least one transcriptional regulatory sequence next to at least one restriction endonuclease site, and
  (ii) DNA from a non-essential segment of the poxvirus genome flanking said regulatory sequence and said restriction endonuclease site; and
(b) inserting at least one foreign gene encoding prokaryotic or eukaryotic polypeptides into said restriction endonuclease site next to said transcriptional regulatory sequence.

Intermediate recombinant vectors comprising at least one transcriptional regulatory sequence of the vaccinia major late 11 kDa gene and still lacking a foreign gene encoding prokaryotic or eukaryotic polypeptides are also an object of the present invention and can be prepared by the above step (a) wherein the transcriptional regulatory sequence of the vaccinia major late 11 kDa gene includes the translational inition site of the 11 kDa gene or, optionally, is terminated in the region between the mRNA start and the translational inition site of the 11 kDa gene.

The vector used to assemble the recombinant vector may be any convenient plasmid, cosmid, or phage. Convenient vehicles of plasmid, cosmid or phage origin are mentioned, e.g., in the laboratory manual "Molecular Cloning" by Maniatis et al., Cold Spring Harbor laboratory, 1982. Preferred vectors of plasmid origin used to assemble the recombinant vectors in this invention are pBR322 and pUC8.

The DNA used to flank the chimeric gene may be derived from non-essential regions of the poxvirus genome. Examples of such non-essential regions include the thymidine kinase (TK) gene (J. P. Weir and B. Moss, J. Virol. 46, 530–537 [1983]). The preferred non-essential regions used in this invention comprise a segment of the poxvirus thymidine kinase gene and DNA adjacent to said thymidine kinase gene. Especially preferred is a segment of the vaccinia virus thymidine kinase gene and vaccinia DNA adjacent to said vaccinia thymidine kinase gene. The preparation of the non-essential regions is described more in detail in Example 1.

Foreign genes that may be inserted into the recombinant vectors of this invention may be selected from a large variety of genes (DNA genes or DNA copies of RNA genes) that encode prokaryotic or eukaryotic polypeptides. For example, such genes may encode enzymes, hormones, polypeptides with immunomodulatory, anti-viral or anti-cancer properties, antibodies, antigens, and other useful polypeptides of prokaryotic or eukaryotic origin. Examples of such genes include but are not limited to genes encoding interleukin-2, an HTLV-III envelope protein, growth hormone releasing factor and a malaria antigen. Preferred foreign genes used in this invention are the genes encoding malaria antigens, in particular the 5.1 surface antigen of *Plasmodium falciparum* (Hope, I.A. et al., infra) and the mouse dihydrofolate reductase (DHFR) gene (A.C.Y. Chang et al., "Phenotypic expression in *E. coli* of a DNA sequence coding for mouse dihydrofolate reductase", Nature 275, 617–624 [1978]).

Plasmids of the pHGS family are specific examples of plasmid recombinant vectors of the present invention. Their preparation is described more in detail in Examples 1–4. *E. coli* strains containing plasmids useful for the preparation of the recombinant vectors of the present invention (*E. coli* HB101 transformed with pHGS-1; pHGS-2) were deposited at Deutsche Sammlung von Mikroorganismen (DSM) in Göttingen on Feb. 21, 1985 the accession Nos. being DSM 3248 and DSM 3249, respectively. Other gram-negative hosts such as *E. coli* C 600 (*E. coli* DH 1) and *E. coli* RR1 (ATCC No. 31343) can also be used and are described in the laboratory manual "Molecular Cloning" by Maniatis et al., supra.

Suitable recombinant infectious poxviruses containing and expressing the above mentioned chimeric genes can be obtained by methods well known in the art (G. L. Smith et al., Biotechnology and Genetic Engeneering Reviews 2, 383–407 [1984]; M. Mackett et al., supra) comprising the steps of:

(a) providing at least one cell infected with a genus of poxvirus;
(b) transfecting said cell with a recombinant vector, whereby homologous recombination occurs between the DNA of the poxvirus and at least one portion of the poxvirus DNA contained in the recombinant vector; and
(c) isolating from said cell a recombinant infectious poxvirus capable of expressing said foreign gene encoding prokaryotic or eukaryotic polypeptides by selective methods.

Suitable eukaryotic host organisms which can be used for the manufacture of a recombinant infectious poxvirus include CV-1, RK-13, TK$^-$143 or other cells. The preferred eukaryotic host cell used in this invention is RK-13.

Recombinant infectious vaccinia viruses RVV 1 through 8 are specific examples of the present invention. Details of their preparation and isolation are indicated in Examples 1–4.

Examples of proteins which can be expressed by using the recombinant infectious vaccinia viruses of the present invention are mouse dihydrofolate reductase, chloramphenicol acetyltransferase and malaria surface antigens, in particular the 5.1 surface antigen of *Plasmodium falciparum*.

Methods for expressing chimeric genes encoding prokaryotic or eukaryotic polypeptides using recombinant infectious poxviruses are well known. (G. L. Smith et al., supra; M. P. Kieny et al., Nature 312, 163–166 [1984]; G. L. Smith et al., Science 224, 397–399 [1984]; E. Paoletti et al., Proc. Natl. Acad. Sci. U.S.A. 81, 193–197 [1984]; D. Panicali et al., supra). They include infecting an appropriate host with a recombinant infectious poxvirus having the desired foreign gene operatively linked to the poxvirus transcriptional regulatory sequence, incubating the host under appropriate conditions and detecting the desired polypeptide by immunological, enzymatic or electrophoretic methods.

The recombinant infectious poxviruses can therefore be used as live vaccines by inoculating an animal or human with an inoculant containing a concentration of said recombinant infectious poxvirus sufficient to elicit an immunological response in said animal or human comprising the production of antibodies to at least the antigenic portion of the protein encoded by said foreign gene. Preferred recombinant infectious poxviruses used in this invention for protective immunization are recombinant infectious vaccinia viruses. Especially preferred are those expressing malaria surface antigens, in particular the 5.1 surface antigen of *Plasmodium falciparum*.

The recombinant infectious poxviruses of the invention can also be used as sources for the continuous in vivo production of other polypeptides or proteins in animals or in human beings. For example, genes encoding interleukin-2, HTLV-III envelope protein or growth hormone releasing factor could be inserted into such poxvirus carriers.

Recombinant infectious vaccinia viruses for use in man can be prepared as described by C. Kaplan (Br. med. Bull. 25, 131-135 [1969]). Preparations suitable for vaccination must contain $10^6$ to $10^8$ plaque forming units per 0.05 ml. The vaccine can be stored frozen in aqueous buffer solution containing 40-50% glycerol, or in lyophilized form. This lyophilized form of the vaccine is essential for use in underdeveloped areas. Vaccination is achieved as a result of intradermal inoculation. A drop of the vaccine is applied to a small sterilized area of the skin and the epidermis beneath is then rapidly punctured by means of a sharp sterile needle or knife. In mass vaccination compaigns jet guns are used.

EXAMPLES

The methods used in the following nonlimiting examples were performed as described by Maniatis et al., supra, unless indicated differently: Restriction endonuclease digestions at 37° C. (pp. 100-101); dephosphorylation with bacterial alkaline phosphatase (BAP) at 37° C. (pp. 133-134); ligation with T4 DNA ligase at 14° C. (pp. 390-391); transformation of DNA into CaCl$_2$-cells of *E. coli* HB101 and selection of transformants on agar plates containing LB-medium plus 100 μg/ml ampicillin (pp. 250-251); DNA plasmid preparation (pp. 86-94); filling-in single-stranded DNA-tails with the large fragment of DNA polymerase I (Klenow fragment) at 14° C. (pp. 113-114); DNA separation and fragment purification from agarose gels (pp. 164-167); the use of synthetic DNA linkers in subcloning (pp. 392-397); removal of single-stranded DNA-tails with nuclease S1 at room temperature (p. 140); isolation of mRNA from mammalian cells (pp. 191-193); nuclease-S1 mapping of mRNA (pp. 207-209); sequencing of DNA by the Maxam-Gilbert technique (pp. 475-478).

Cultured cells used were as follows: Rabbit kidney (RK-13) (Christofinis, G. J. and Beale, A. J., J. Path. Bact. 95, 377-381 [1968]); human osteosarcoma cells transformed with murine sarcoma virus (Human TK⁻ 143 cells repository no. GM 5887, Human genetic mutant Cell Repository, Institute for Medical Research, Copewood St., Camden, N.J. 08103, USA). Maintenance of cells was at the indicated temperature in Eagle's minimal essential medium (E-MEM) supplemented with 5% fetal calf serum and 100 μg/ml of streptomycin and 100 IU/ml of penicillin at 80% humidity and 5% CO$_2$.

EXAMPLE 1

Figure 1B:
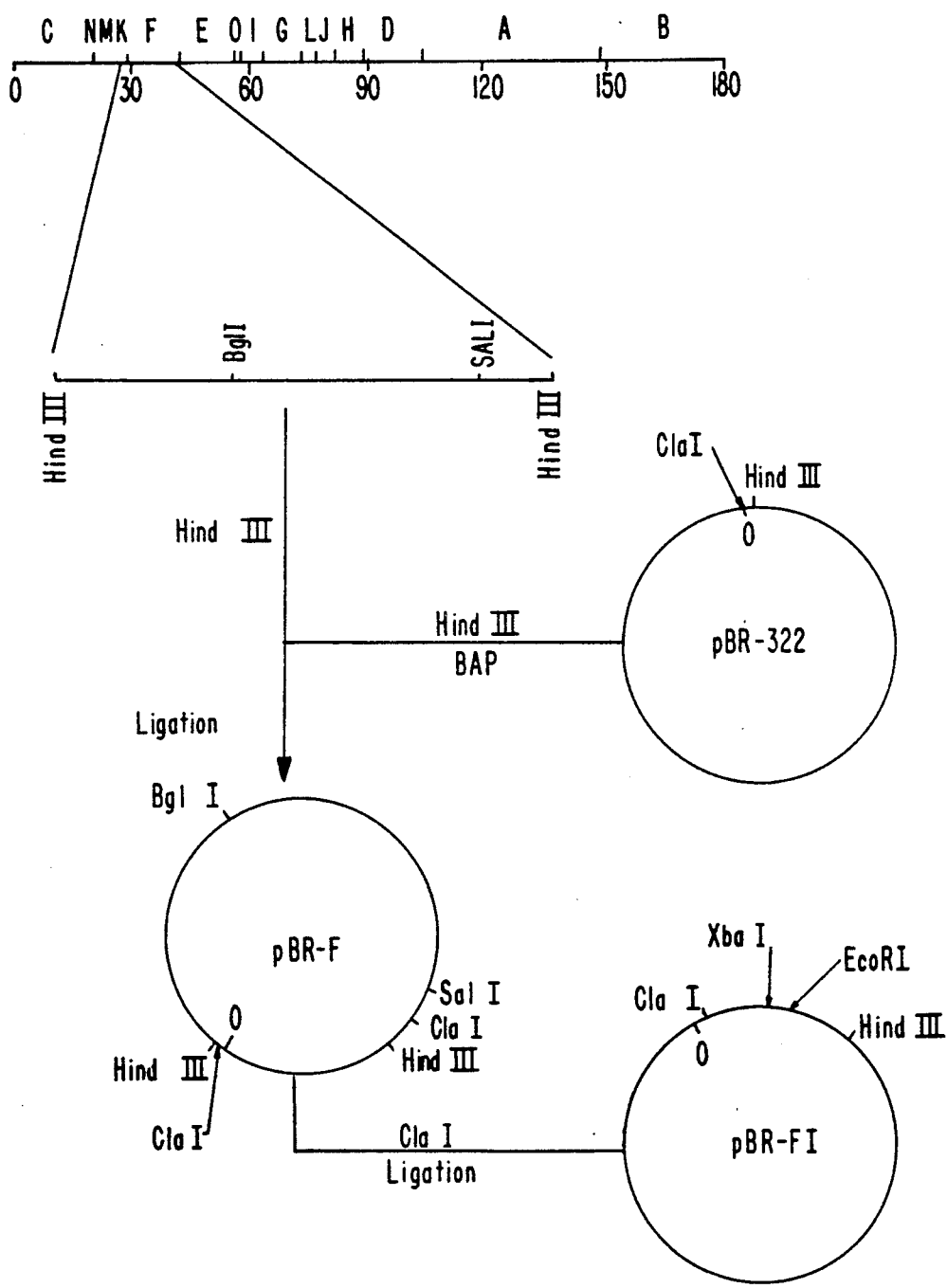

Construction of Recombinant Vaccinia Virus RVV-1 Carrying the 11 kDa Transcriptional Regulatory Sequence A. Construction of Plasmids pBR-J and pBR-F1 (FIG. 1a and 1b)

Ten μg of Vaccinia virus (VV) DNA (WR strain) were digested to completion with 100 units of the restriction endonuclease HindIII. The HindIII J-fragment (approx. 5 kb) containing the VV thymidine kinase (TK) gene (Weir, J. P. and Moss, B., J. Virology 46, 530-537 [1983]) and F-fragment (approx. 14 kb) were isolated from agarose. One μg of the plasmid pBR-322 (J. G. Sutcliffe, "Complete Nucleotide Sequence of the *Escherichia coli* Plasmid pBR-322", Cold Spring Harbor Symp. Quant. Biol. 43, pp 77-90 [1979]) was digested with one unit of the restriction endonuclease HindIII to completion, and free ends were dephosphorylated with one unit of bacterial alkaline phosphatase (BAP) for 1 hour. Twenty ng of HindIII linearized pBR-322 and 100 ng of the HindIII J-fragment (FIG. 1a) or 100 ng of the HindIII F fragment (FIG. 1b) were ligated with one unit of T4 DNA ligase and transformed into *E. coli* HB101 cells. In each case four transformants resistant to ampicillin were selected, and cultures were grown in LB-medium containing 100 μg/ml ampicillin. DNA from these cultures was isolated using standard procedures and analyzed for size and for the presence of sites for the restriction endonucleases HindIII, EcoRI and KpnI in the case of the J-fragment and HindIII, SalI and BglI in the case of the F-fragment. Plasmids displaying the expected patterns after electrophoresis in agarose gels were designated pBR-J and pBR-F, respectively.

One μg of the plasmid pBR-F was digested to completion with 2 units of the restriction endonuclease ClaI, the DNA was loaded on a 0.8% agarose gel and a fragment of 5.6 kb (consisting of the plasmid pBR-322 and 1.25 kb of the insert) was isolated as described. Fifty ng of this plasmid were religated using 1 unit of T4 ligase, and the DNA was transformed into HB101 as described. Four transformants that were resistant to ampicillin were selected, and cultures were grown in LB-medium containing 100 μg/ml ampicillin. DNA from these cultures was isolated using standard procedures and analyzed for size and for the presence of sites for the restriction endonucleases HindIII, ClaI and EcoRI. One plasmid displaying the expected patterns after electrophoresis in agarose gels was designated pBR-F1.

Figure 2:
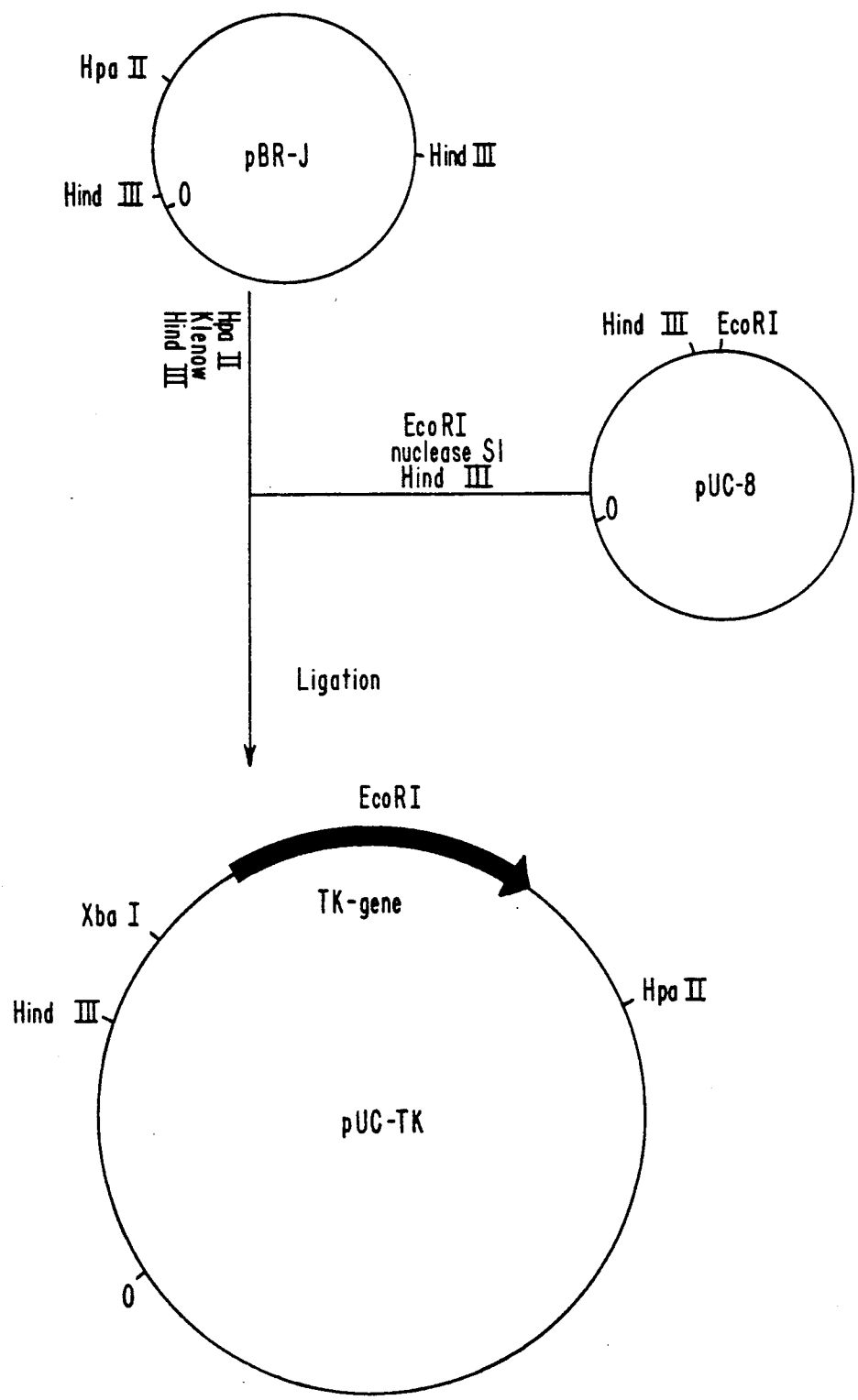
FIG. 2 is a schematic outline of the subcloning of the vaccinia virus TK-gene plus flanking sequences into plasmid pUC-8 resulting in plasmid pUC-TK.

B. Construction of Plasmid pUC-TK (FIG. 2)

Two μg of the plasmid pBR-J were digested to completion with 5 units of the restriction endonuclease HpaII, and single-stranded DNA-tails were filled in with 4 units of the large fragment of DNA polymerase I (Klenow fragment). The DNA was subsequently digested to completion with 5 units of the restriction endonuclease HindIII, the DNA was separated in a 0.8% agarose gel and a DNA fragment of 1310 bp was isolated from the agarose gel. Two μg of the plasmid pUC-8 (J. Vierra and J. Messing, "The pUC Plasmids, an M13mp7-derived System for Insertion Mutagenesis and Sequencing with Synthetic-universal Primers", Gene 19, pp 259-268 [1982]) were digested to completion with 5 units of the restriction endonuclease EcoRI, and single-stranded DNA-tails were removed with 2 units of nuclease S1 for 1 hour at room temperature in S1 buffer. This DNA was subsequently digested to completion with 5 units of the restriction endonuclease HindIII, the free ends were dephosphorylated with 2 units of BAP for 1 hour, the DNA was separated in a 0.8% agarose gel and a fragment of 2.7 kb was isolated from the agarose as previously described. Fifty ng of this pUC-8 fragment were ligated with 200 ng of the purified 1310 bp VV fragment using one unit of T4 DNA ligase and the ligated DNA was transformed into HB101. Eight transformants that were resistant to ampicillin were selected, and cultures were grown in LB-medium containing 100 µg/ml ampicillin. DNA from these cultures was isolated using standard procedures and analyzed for size and for the presence of sites for the restriction endonucleases HindIII, EcoRI and XbaI. One plasmid displaying the expected patterns after electrophoresis in agarose gels was designated pUC-TK.

Figure 3:
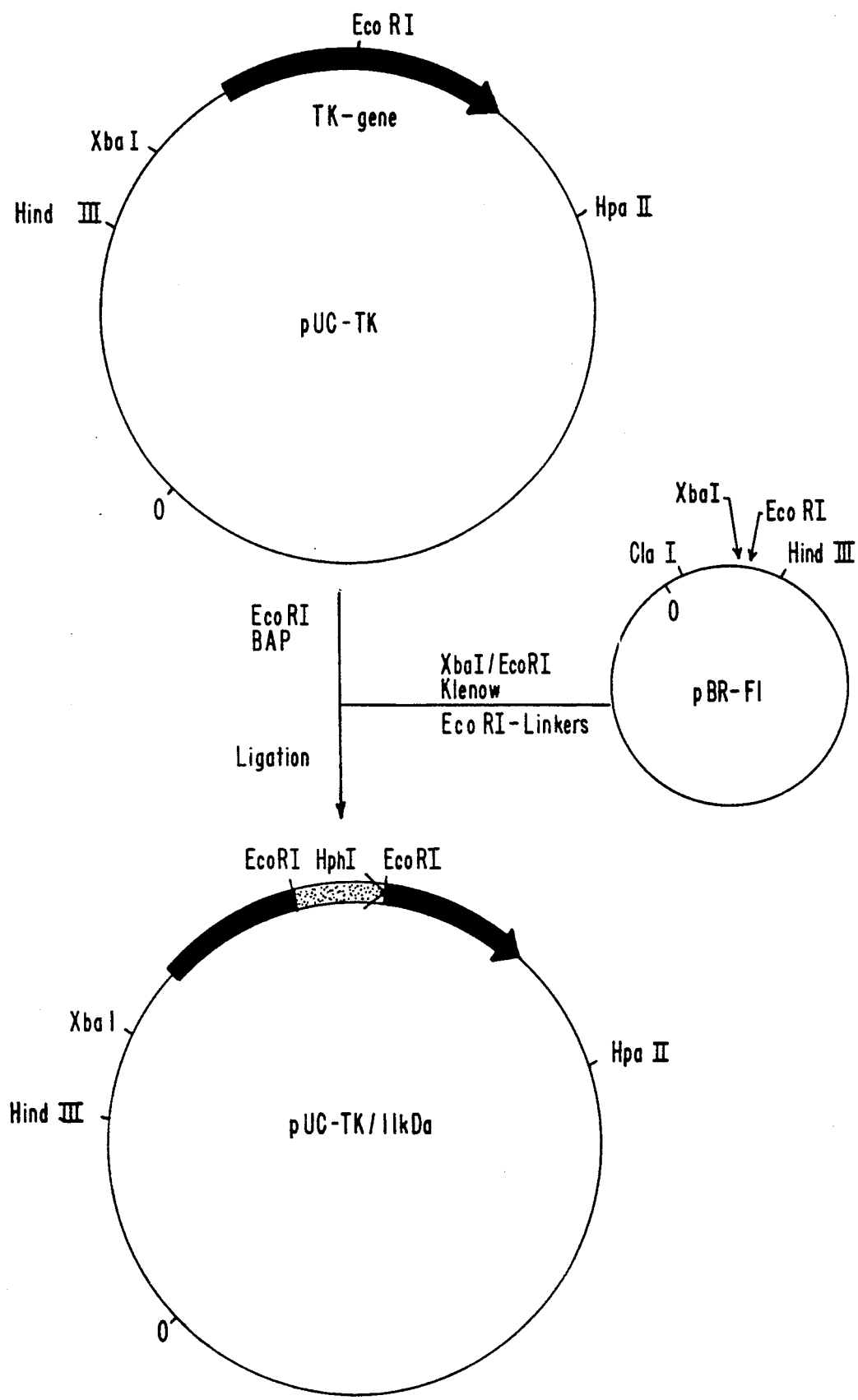
FIG. 3 is a schematic outline of the insertion of the transcriptional regulatory sequences of the 11 kDa protein of vaccinia virus into the TK-gene resulting in plasmid pUC-TK/11 kDa.

C. Construction of Plasmid pUC-TK/11 kDa (FIG. 3)

Fifty µg of the plasmid pBR-F1 were digested to completion with 200 units each of the restriction endonucleases EcoRI and XbaI, and the DNA was separated in a 1.2% agarose gel. A DNA fragment of 104 bp was isolated, single-stranded DNA-tails were filled in with 4 units of Klenow fragment and synthetic EcoRI linkers (CGAATTCG) were attached. This new DNA fragment with Eco linkers (110 bp) consisted of the 11 kDa transcriptional regulatory sequence of VV. Two µg of the plasmid pUC-TK were digested to completion with 5 units of the restriction endonuclease EcoRI, free DNA-ends were dephosphorylated with 2 units of BAP, the DNA was separated in a 0.8% agarose gel and the linear DNA fragment of 4 kb was isolated and extracted. Fifty ng of the EcoRI linearized pUC-TK vector were ligated using 1 unit of T4 DNA ligase with 10 ng of the 110 bp promoter fragment and transformed into HB101. Eight transformants resistant to ampicillin were selected and cultures were grown in LB-medium containing 100 µg/ml ampicillin. DNA from these cultures was isolated and analyzed for size and for the presence of sites for restriction endonucleases EcoRI and HphI. One plasmid displaying the expected patterns after electrophoresis in 6% acrylamide gels was designated pUC-TK/11 kDa.

Figure 4:
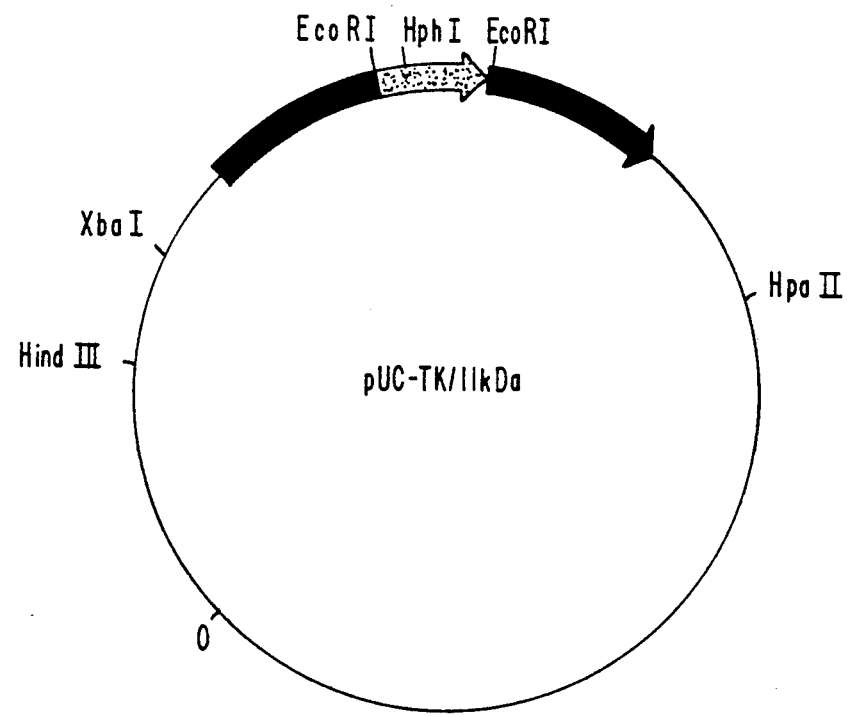
FIG. 4 is a schematic outline of the conversion of the upstream EcoRI restriction endonuclease site of the transcriptional regulatory sequences of the 11 kDa protein into an XmnI restriction endonuclease site resulting in plasmid pHGS-1.
Figure 4:
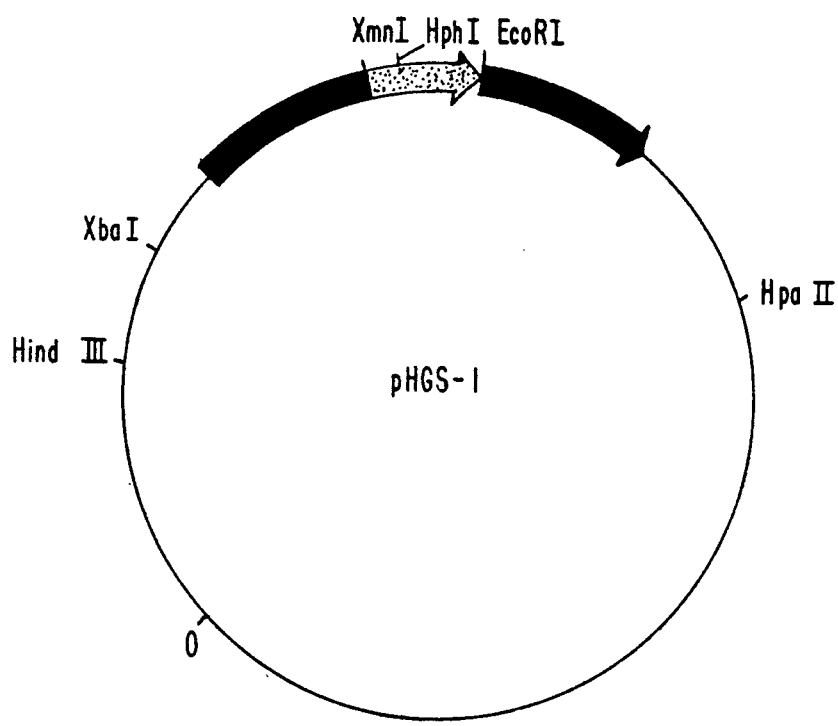

D. Construction of Plasmid pHGS-1 (FIG. 4)

Ten µg of pUC-TK/11 kDa were digested partially (up to 5%) with one unit of the restriction endonuclease EcoRI at 37° C. for 30 min, and single-stranded DNA-tails were filled in with 4 units of Klenow fragment at 14° C. The DNA was separated in a 0.8% agarose gel, the linearized form of the pUC-TK/11 kDa plasmid (4104 bp) was isolated, and 10 ng were self-ligated using 2 units of T4 DNA ligase and transformed into HB101. Sixteen transformants that were resistant to ampicillin were selected, and cultures were grown in LB-medium containing 100 µg/ml ampicillin. DNA from these cultures was isolated and analyzed for size and for the presence of sites for restriction endonucleases EcoRI, XmnI and HindIII. Plasmids displaying the expected patterns after electrophoresis in agarose gel were selected and the ClaI-EcoRI fragment of 148 bp was sequenced. One plasmid displaying the sequence indicated on pages 2 and 3 above and including the site for the restriction endonuclease EcoRI was designated pHGS-1.

E. Construction of Recombinant Vaccinia Virus (RVV-1)

RK-13 cells adapted to 33° C. were infected with 0.1 plaque forming units (pfu) per cell of the vaccinia virus temperature sensitive mutant $t_S7$ (Drillien, R. and Spehner, D., Virology 131, 385–393 [1983]). After 2 hours at the permissive temperature of 33° C., the cells were transfected with a calcium phosphate DNA precipitate as described by Weir et al. (Weir, J. P. et al., Proc. Natl. Acad. Sci. USA. 79, 1210–1214 [1982]). Sixty ng of vaccinia wild type DNA (WR strain), co-precipitated with 20 ng of the appropriate recombinant plasmids (pHGS-1) containing the transcriptional regulatory sequence of the 11 kDa gene of vaccinia virus inserted into the body of the TK gene, were used per $2 \times 10^6$ cells. After two days of incubation at 39.5° C. the cells were disrupted by sonication, and the amount of TK negative (TK−) virus in the progeny was determined by titration on Human-TK−143-cells in the presence of 100 µg/ml bromodeoxyuridine. About a 200-fold increase in virus with a TK− phenotype was found in cells that had been transfected with wild type DNA and the recombinant plasmids over that found in cells that had been transfected with wild type DNA alone. Plaques were picked and the virus was plaque-purified a second time on Human-TK−143-cells in the presence of 30 µg/ml bromodeoxyuridine. Virus stocks were then made on RK-13 cells in the absence of bromodeoxyuridine. The virus RVV-1 was selected for the presence of the 11 kDa promoter inserted into the TK-gene by blot-hybridization (Mackett, M., et al., Proc. Natl. Acad. Sci. USA. 79, 7415–7419 [1982]).

Figure 5A:
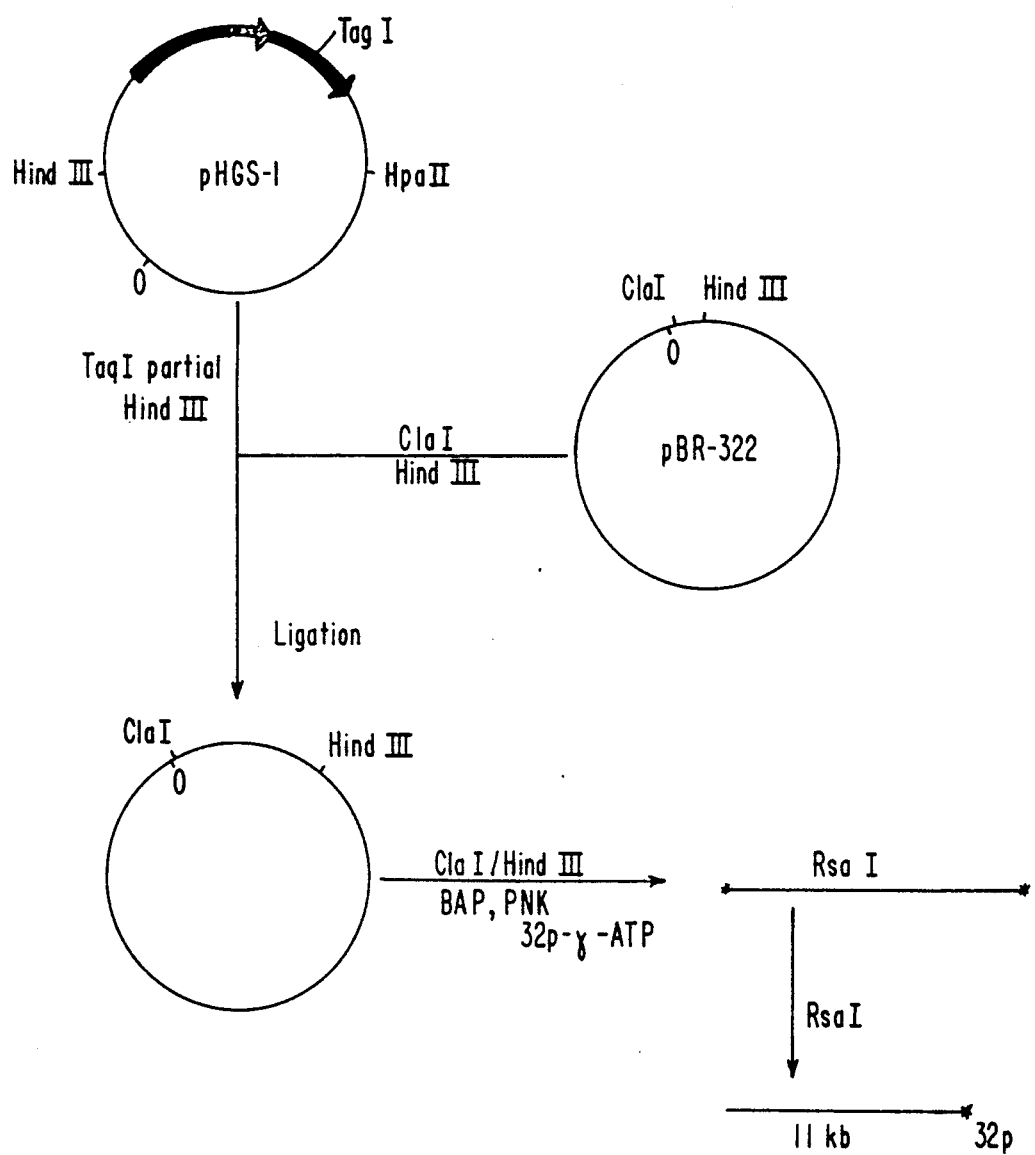
FIG. 5 Part (a) is a schematic outline of the isolation and radioactive labelling of the nuclease S1 probe for transcripts starting at the transcriptional regulatory sequences of the 11 kDa protein inserted into the TK-gene. Part (b) is a schematic outline of the isolation and radioactive labelling of the nuclease S1 probe for transcripts starting at the regulatory sequences of the TK-gene.

F. Cloning and Preparation of the Nuclease S1 Probes a. Nuclease S1 probe for transcripts of the 11 kDa transcriptional regulatory sequence inserted in the TK-gene (FIG. 5a)

Figure 5B:
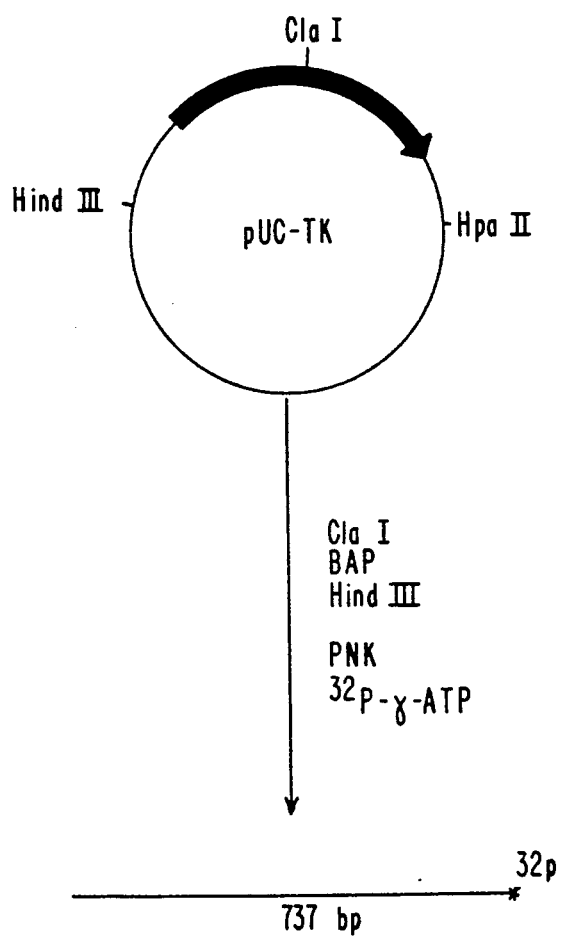
Figure 6:
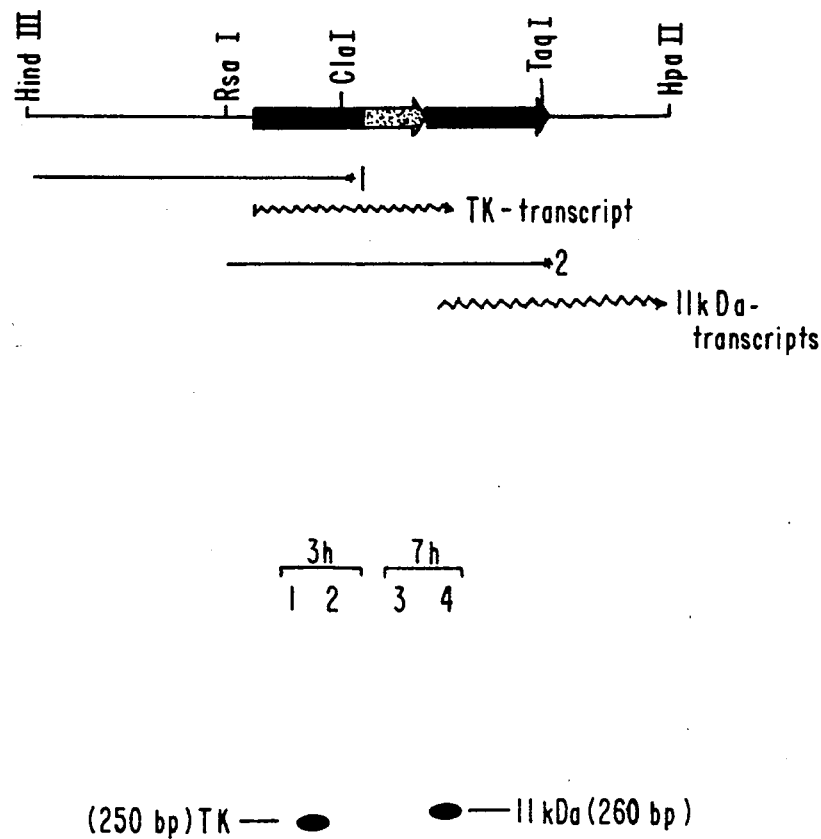
FIG. 6 The upper part is an outline of mapping of RNA transcripts ( ⌇⌇⌇→ ) with nuclease S1. The lower part is the autoradiographic exposure of the nuclease S1 mapping of TK transcript (250 bp) and 11 kDa transcript (260 bp). RNA's from infected cells were harvested at 3 hours (lanes 1 and 2) or at 7 hours (lanes 3 and 4) post infection.

Ten µg of the plasmid pHGS-1 were partially digested (up to 10%) with 2 units of the restriction endonuclease TaqI. The DNA's were subsequently digested to completion with 20 units of the restriction endonuclease HindIII and separated in an agarose gel, and a DNA fragment of 1135 bp was isolated. One hundred ng of this fragment were ligated with 1 unit of T4 DNA ligase with 25 ng of the plasmid pBR-322 that had been digested to completion with 1 unit each of the restriction endonucleases HindIII and ClaI and transformed into HB101. Four transformants resistant to ampicillin were selected, and the cultures were grown in LB-medium containing 100 µg/ml ampicillin. DNA from these cultures was isolated and analyzed for size and for the presence of sites for the restriction endonucleases HindIII, EcoRI and ClaI. Plasmids displaying the expected patterns in agarose gels were selected and used to prepare nuclease S1 DNA probes as follows: Ten µg of the plasmid were digested to completion with 20 units each of the restriction endonucleases ClaI and HindIII, free ends were dephosphorylated with 10 units of BAP, a DNA fragment of 1.6 kb was isolated and 0.1 pmol was labelled before use with 1 unit of polynucleotide kinase (PNK) and 1 pmol of $\gamma$-$^{32}$P-deoxyadenosine triphosphate, and the DNA was subsequently digested to completion with 1 unit of the restriction endonuclease RsaI.

b. Nuclease S1 probe for TK transcripts (FIG. 5b)

Five µg of the plasmid pUC-TK were digested to completion with the restriction endonuclease ClaI, free ends were dephosphorylated with 5 units BAP, and the DNA was subsequently digested to completion with the restriction endonuclease HindIII. The DNA was then separated in 0.8% low melting agarose, and a DNA fragment of 737 bp was isolated. The S1 probe was labelled with PNK and $\gamma$-$^{32}$P-deoxyadenosine triphosphate as previously described.

G. 5′ S1 Mapping of the RNA Transcripts

Two petri dishes (5 cm diameter) with a confluent monolayer of RK-13 cells were each infected with 10 pfu per cell of the recombinant virus RVV-1, and after 3 or 7 hours the RNA was extracted. The RNA's were resuspended in 100 $\mu$l of 0.2% SDS, divided into two equal parts and 20,000 cpm of the $^{32}$P-labelled S1 probe for the TK-gene or the 11 KDa gene transcriptional regulatory sequence were added. The different mixtures were then precipitated with 1/10 volume of NaOAc and 2½ volumes of ethanol. The pellet was redissolved in 50 $\mu$l of S1 hybridisation buffer, heated for 3 minutes at 100° C. and incubated for 16 hours at 42° C. before addition of 450 $\mu$l of one times nuclease S1 buffer and 25 units of the enzyme nuclease S1. The digestion was stopped after one hour with EDTA (final concentration of 50 mM) and SDS (final concentration of 0.5%). Sodium hydroxide was added to a final concentration of 0.25N, and after 1 hour at 45° C. the mixture was neutralized to pH 7 using 3M HOAc. The residual DNA was precipitated using 5 $\mu$g of tRNA as a carrier, washed with 80% ethanol and dissolved in 20 $\mu$l of formamide loading buffer, and 10 $\mu$l were loaded on a 8% acrylamide-8M urea sequencing gel. The gel was exposed for 24 hours using Kodak x-ray film and an intensifying screen. The results of this autoradiographic exposure shown in FIG. 6. At 3 hours post infection, only transcripts from the TK-promoter could be detected (slot 1), whereas at 7 hours after infection a strong S1 protected band could be detected starting at the inserted 11 kDa promoter (260 bp), with only trace amounts of the TK-transcripts. Therefore, it could be concluded that the inserted 11 kDa regulatory sequence was functioning late after infection.

EXAMPLE 2

Construction of Recombinant Vaccinia Virus RVV-2 and RVV-3 Carrying Subunits of the 11 kDa Transcriptional Regulatory Sequence of VV A. Constructions of Plasmids pHGS-2 and pHGS-2Δ15

Three $\mu$g of the plasmid pHGS-1 were digested to completion with 10 units of the restriction endonuclease EcoRI, and the DNA was incubated at 37° C. with 1 unit of T4 DNA polymerase in T4 polymerase buffer (Maniatis et al., supra) with deoxythymidine triphosphate at a final concentration of 100 $\mu$M. After 30 minutes the reaction was stopped by heating at 65° C. for 10 minutes. The mixture was diluted 10-fold with nuclease S1 buffer, and single-stranded DNA-tails were removed with 2 units of nuclease S1 for 1 hour. Synthetic BamHI linkers (5′-AAAGGATCCTTT-3′) were ligated to the blunt DNA-ends and 100 ng of the DNA was self-ligated with 1 unit of T4 DNA ligase and digested with 10 units of the restriction endonuclease EcoRI for 1 hour and transformed into HB101. Eighty transformants resistant to ampicillin were selected and cultures were grown in LB-medium containing 100 $\mu$g/ml ampicillin. DNA from these cultures was isolated and analyzed for size and for the presence of a site for restriction endonuclease BamHI. DNA's containing a site for the restriction endonuclease BamHI were selected. From each of these DNA's 20 $\mu$g were digested to completion with 50 units each of the restriction endonucleases BamHI and ClaI. The DNA's were separated in acrylamide gels and DNA fragments of 156 and 141 bp were isolated and sequenced using the Maxam-Gilbert technique after labelling the fragments at the site of the restriction endonuclease BamI using 1 unit of Klenow fragment and $\alpha$-$^{32}$P-deoxyguanidine triphosphate. DNA's were selected having the following sequence preceeding the sequence 5′-AAAGGATCC-3′ (representing the BamHI linker):

No. 1: 5′ - CTAGA AGCGA TGCTA CGCTA GTCAC
AATCA CCACT TTCAT ATTTA GAATA TATGT ATGTA
AAAAT ATAGT AGAAT TTCAT TTTGT TTTTT TCTAT
GCTAT AAAT - 3′

No. 2: 5′ - CTAGA AGCGA TGCTA CGCTA GTCAC
AATCA CCACT TTCAT ATTTA GAATA TATGT ATGTA
AAAAT ATAGT AGAAT TTCAT TTTGT TTTTT - 3′

Five $\mu$g of the DNA's having the sequence No. 1 or 2 were digested to completion with 10 units each of the restriction endonucleases BamHI and HindIII. The DNA was separated in an agarose gel and DNA fragments of 888 and 873 bp were isolated, and 100 ng of each were ligated with a 50-molar excess each of the synthetic DNA fragments 5′-GATCCCCGGG-3′ and 5′-AATTCCCGGG-3′ using 1 unit of T4 DNA ligase. The DNA was subsequently digested with 300 units of the restriction endonuclease EcoRI for 8 hours, loaded on a 6% acrylamide gel and fragments of 898 and 883 bp were isolated.

Two $\mu$g of the plasmid pHGS-1 were digested to completion with 5 units each of the restriction endonucleases EcoRI and HindIII, the DNA was separated in an agarose gel and a fragment of 3.2 kb was isolated. Twenty five ng of this 3.2 kb fragment were ligated with 50 ng of the 898 or 883 DNA fragments using 1 unit of T4 DNA ligase, and the DNA's were transformed into HB101. In each case 4 transformants that were resistant to ampicillin were selected, and the cultures were grown in LB-medium containing 100 $\mu$g/ml ampicillin. DNA from these cultures was isolated and analyzed for size and for the presence of sites for restriction endonucleases EcoRI, SmaI and BamHI. In each case one plasmid displaying the expected patterns after electrophoresis in agarose gels was designated pHGS-2 (containing sequence No. 1) or pHGS-2Δ15 (sequence No. 2).

B. Construction of Recombinant Virus RVV-2 and RVV-3

The recombinant viruses RVV-2 and RVV-3 were constructed as described before using the plasmids pHGS-2 or pHGS-2Δ15. In each case one virus was selected for the presence of the mutated 11 kDa transcriptional regulatory sequence (No. 1 or 2) inserted into the TK-gene by blot-hybridization (Mackett et al., supra).

C. Cloning of the Nuclease S1 Probes

The preparation of the nuclease S1 probes for transcripts of the transcriptional regulatory sequence No. 1 or No. 2 inserted into the TK-gene was as described in Example 1, Section F.a., using the plasmids pHGS-2 or pHGS-2Δ15.

D. 5' S1 Mapping of the RNA Transcripts

Figure 7:
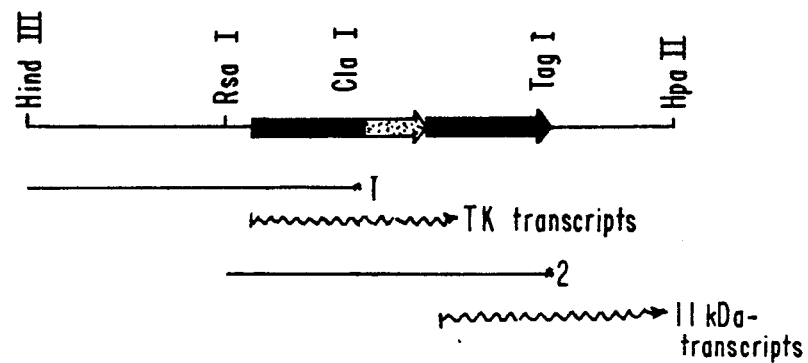
FIG. 7 The upper part represents an outline of the mapping of RNA transcripts ( ⌇⌇⌇→ ) with nuclease S1. The lower part is the autoradiographic exposure of the nuclease S1 mapping of RNA transcripts from cells infected with RVV-2 (pHGS-2, lane 1 and 2) resp. RVV-3 (pHGS-2Δ15, lane 3 and 4). RNA was extracted at 4 hours (lane 1 and 4) resp. 8 hours (lane 2 and 3) post infection. Lanes marked "M" consist of $^{32}$P-labelled HpaII fragments of pBR-322 giving the length position (in bp) as indicated. The position of the S1 protected band corresponding to RNA transcripts starting at the regulatory sequences of the TK-gene or the inserted 11 kDa gene are indicated.
Figure 7:
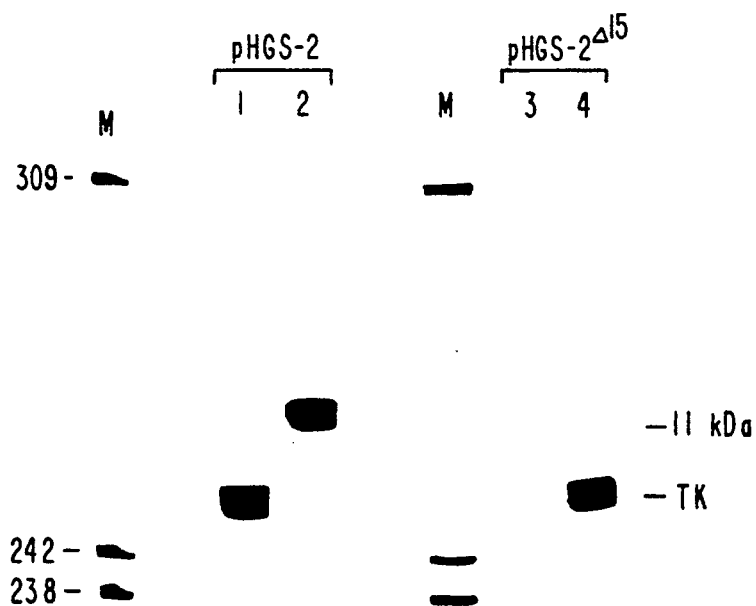

RNA transcripts 4 or 8 hours after virus infection were prepared as described previously using the viruses RVV-2 or RVV-3 and the S1 probes for RNA transcripts from the TK promoter or the 11 kDa transcriptional regulatory sequences (containing sequences No. 1 or 2). The autoradiographic exposure is shown in FIG. 7. At 4 hours post infection (slots 1 and 4) only transcripts from the TK promoter could be detected. These transcripts were undetectable at 8 hours post infection, whereas with cells infected with the virus RVV-2 (pHGS-2 inserted), a strong S1 protected band could be detected. However with RVV-3 (pHGS-2Δ15 inserted) no S1 protected band appeared, demonstrating that the deletion of 15 basepairs 5' from the ATG resulted in an inactivation of transcripts starting from the mutated transcriptional regulatory sequence.

EXAMPLE 3

Construction of Recombinant Vaccinia Virus RVV-4 and RVV-5 Containing the Merozoite 5.1 Surface Antigen Operatively Linked to the 11 kDa Transcriptional Regulatory Sequence of VV

Figure 8:
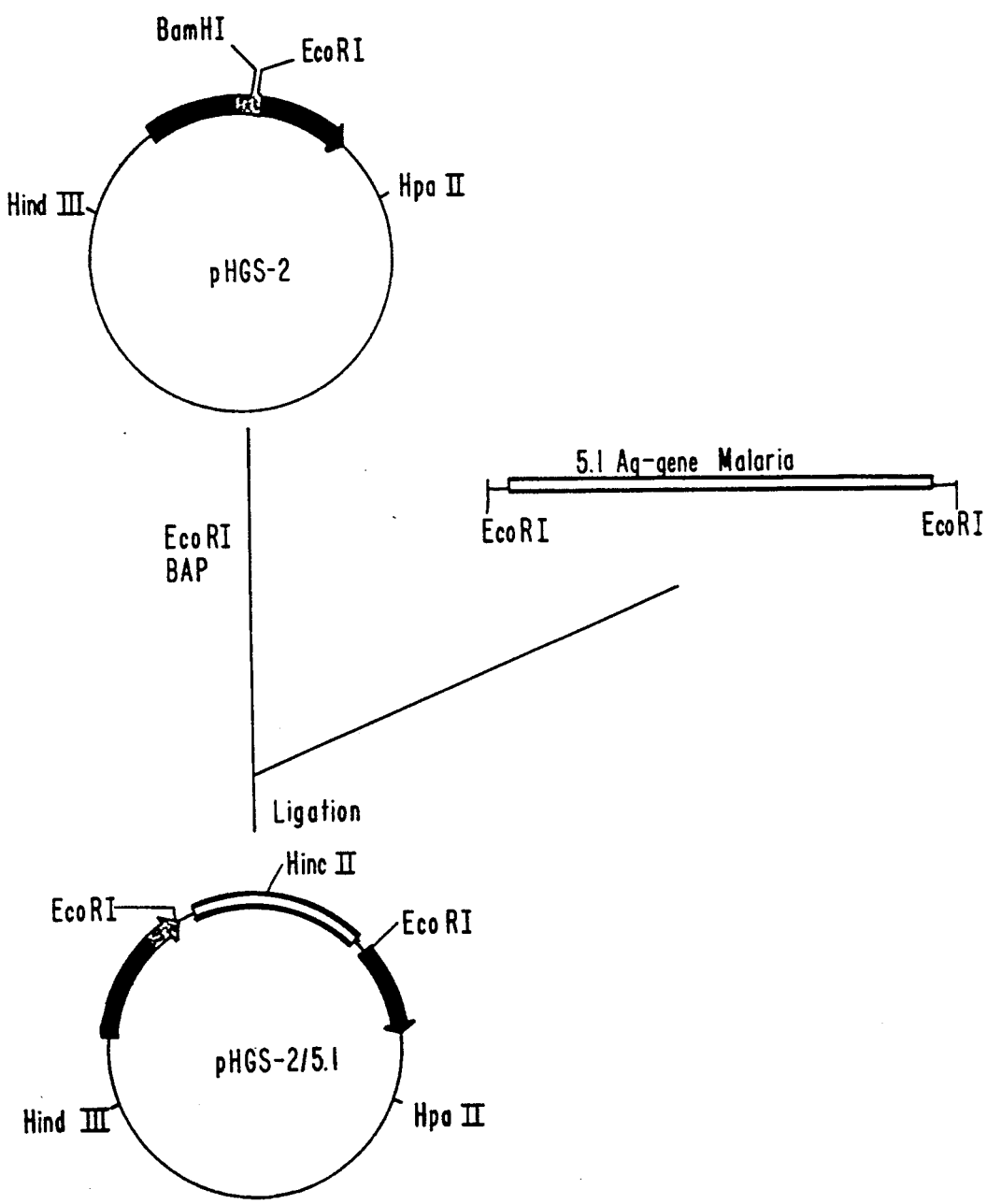
FIG. 8 represents a schematic outline of the cloning of the *Plasmodium falciparum* 5.1 antigen (Hope et al. supra) into the plasmid pHGS-2 resulting in the plasmid pHGS-2/5.1.

A. Cloning of Plasmodium falciparum 5.1 Antigen (FIG. 8)

One hundred ng of a *Plasmodium falciparum* cDNA fragment with flanking EcoRI linkers containing the merozoite 5.1 surface antigen of *Plasmodium falciparum* (Hope, I.A. et al., Nucleic Acids Research, 13, 369–379 [1985]) were ligated using 1 unit of T4 DNA ligase into 50 ng of pHGS-2 or pHGS-2Δ15 and digested to completion with the restriction endonuclease EcoRI, after which the free ends were dephosphorylated using 1 unit of BAP. The ligated DNA's were subsequently transformed into HB101, and in each case four transformants that were resistant to ampicillin were selected and cultures were grown in LB-medium containing 100 μg/ml ampicillin. DNA from these cultures was isolated and analyzed for size and for the presence of sites for the restriction endonucleases EcoRI and HincII. In each case one plasmid displaying the expected patterns after electrophoresis in agarose gels was designated pHGS-2/5.1 or pHGS-2Δ15/5.1.

B. Construction of Recombinant Vaccinia Virus RVV-4 and RVV-5

The recombinant viruses RVV-4 and RVV-5 were constructed and selected as described before using the plasmids pHGS-2/5.1 and pHGS-2Δ15/5.1.

C. Indirect Immunofluorescence

RK-13 cells were grown to 80% confluency and infected with 0.1 pfu per cell of recombinant vaccinia virus RVV-4 or RVV-5, with the malaria 5.1 antigen stably integrated into the virus genome through homologous recombination. One hour after infection the cells were washed with phosphate buffered saline (PBS), and fresh medium was added to the cells. Infection with the virus was allowed to continue for an additional 16 hours. Cells were then scraped from the culture dishes, harvested through centrifugation at 2000 xg and washed once with PBS. Approximately $10^4$ cells were spotted on a microscope glass, air dried, fixed with $-20°$ C. acetone for 10 minutes and again air dried. The fixed cells were incubated at 37° C. for 20 minutes with rabbit anti-5.1 antigen diluted in PBS, washed 3 times with PBS and then air dried again. Next the fixed cells were incubated at 37° C. for 20 minutes with goat anti-rabbit FITC serum diluted with PBS, washed 3 times with PBS, once with distilled water and air dried. PBS-glycerin (1:1) was spotted on the cells and covered with a microscope cover-glass. The cells were analyzed for fluorescence under a microscope illuminated at 450–490 nm, with the result shown in FIG. 9. Panel A shows fluorescent cells infected with the virus RVV-4, while panel B shows infected cells under visible light. Cells infected with the virus RVV-5 did not show any fluorescence, demonstrating that deletions upstream of the 11 kDa-ATG cause inactivation of the regulatory sequences. Removal of the G residue of the ATG, however, had no effect on transcription or translation.

EXAMPLE 4

Construction of Recombinant Vaccinia Virus RVV-6, RVV-7 and RVV-8 Containing the Mouse Dihydrofolate Reductase Operatively Linked to Mutated 11 KDa Transcriptional Regulatory Sequences of VV

Figure 10:
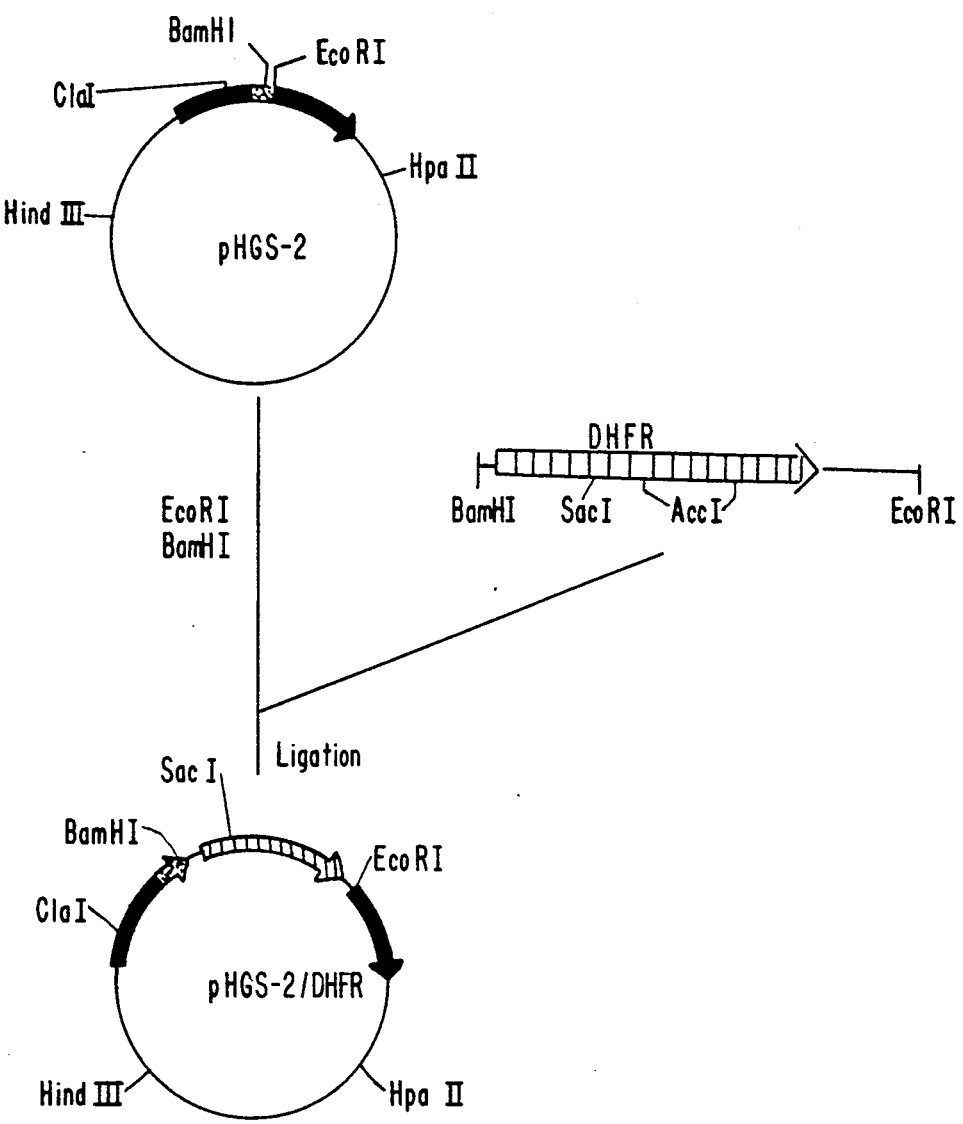
FIG. 10 represents a schematic outline of the construction of plasmid pHGS-2/DHFR.

A. Construction of Plasmid pHGS-2/DHFR (FIG. 10)

Two μg of the plasmid pHGS-2 were digested to completion with 2 units each of the restriction endonucleases BamHI and EcoRI. The DNA was separated in a 0.8% agarose gel and the BamHI-EcoRI vector was isolated (~4 kb).

Two μg of the plasmid pDS-1, to 1+ (deposited at Deutsche Sammlung von Mikroorganismen (DSM) in Göttingen on Dec. 11, 1984, accession No. DSM 3135) were digested to completion with two units each of restriction endonucleases BamHI and EcoRI, and a fragment of approximately 920 bp containing the mouse dihydrofolate reductase (DHFR) gene was isolated. Twenty μg of the BamHI and EcoRI digested vector pHGS-2 and 100 μg of the BamHI-EcoRI fragment containing the mouse dihydrofolate reductase gene were ligated using 1 unit of T4 DNA ligase, and the DNA was transformed into HB101. Eight transformants that were resistant to 100 μg/ml ampicillin were selected, and cultures were grown in LB-medium containing 100 μg/ml ampicillin. DNA from these cultures was isolated and analyzed for size and for the presence of sites for the restriction endonucleases EcoRI, BamHI and SacI. One plasmid displaying the expected patterns was designated pHGS-2/DHFR.

Figure 11:
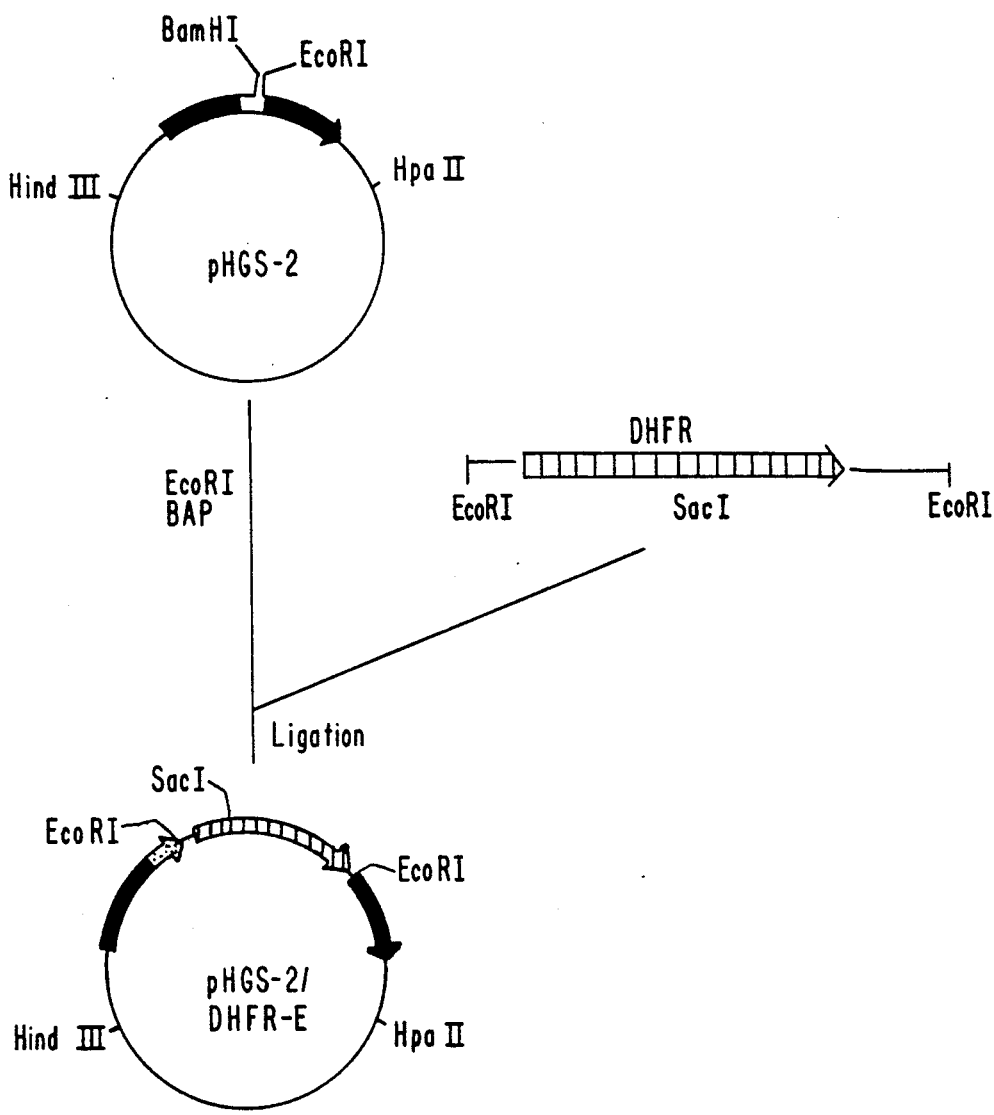
FIG. 11 represents a schematic outline of the construction of plasmid pHGS-2/DHFR-E.

B. Construction of Plasmid pHGS-2/DHFR-E (FIG. 11)

Two μg of the plasmid pHGS-2 were digested to completion with two units of the restriction endonuclease EcoRI, the free ends were dephosphorylated with one unit of bacterial alkaline phosphatase (BAP), and the EcoRI digested vector was isolated from low-melting (LM) agarose. Two μg of the plasmid pDS-1, to 1+ were digested to completion with two units of the restriction endonuclease EcoRI, and a fragment of approximately 920 bp containing the mouse DHFR-gene was isolated from LM agarose. Twenty μg of the EcoRI digested vector pHGS-2 and 100 μg of the EcoRI-fragment were ligated with one unit of T4 DNA ligase, and the DNA was transformed into HB101. Eight transformants that were resistent to 100 μg/ml ampicillin were selected, and cultures were grown in LB-medium containing 100 μg/ml ampicillin. DNA from these cultures was isolated and analyzed for size and for the presence of sites for restriction endonucleases EcoRI and SacI. One plasmid displaying the expected patterns after electrophoresis in agarose gels was designated pHGS-2/DHFR-E (FIG. 11).

Figure 12:
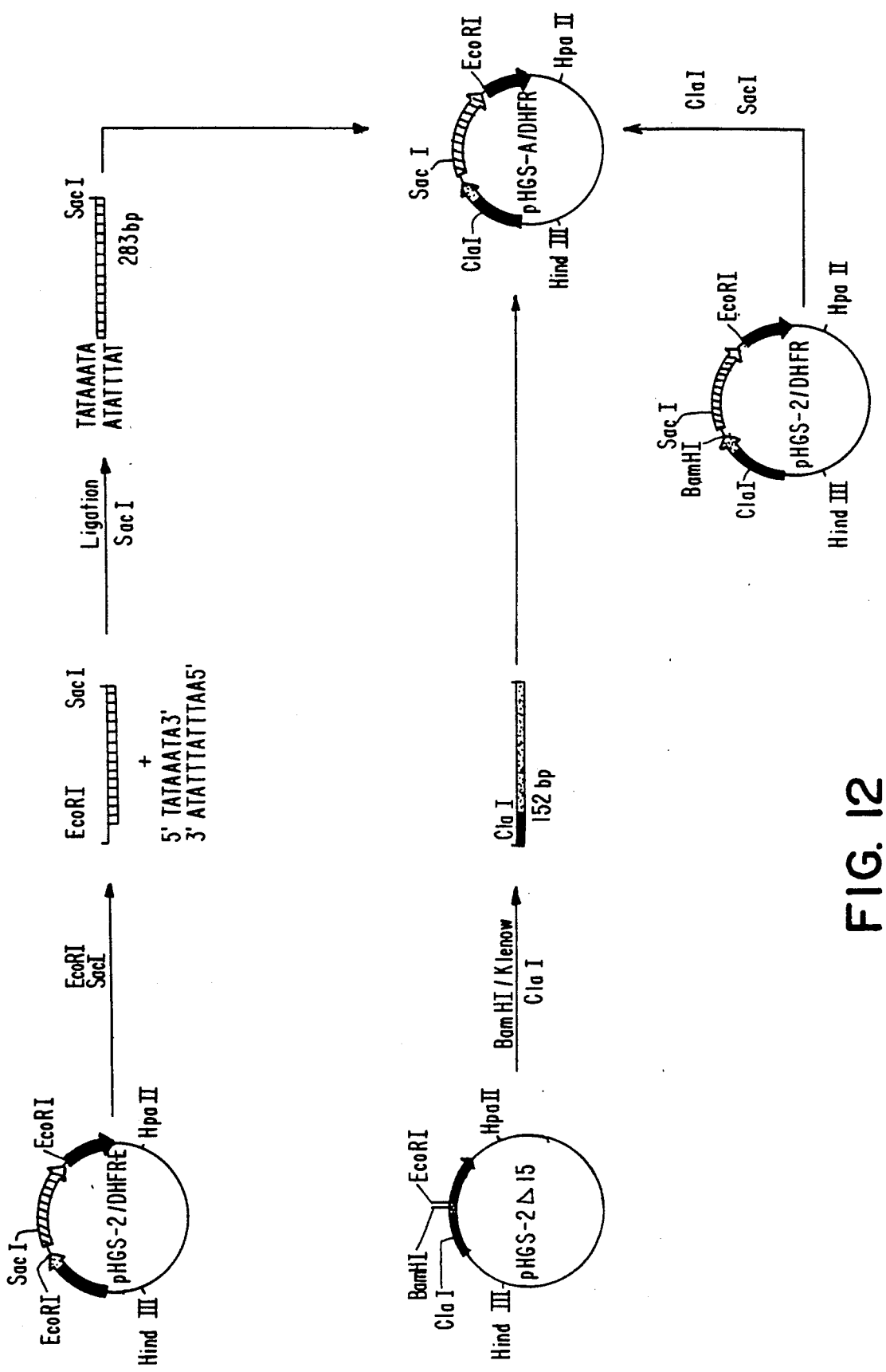
FIG. 12 represents a schematic outline of the construction of plasmid pHGS-A/DHFR.

C. Construction of Plasmid pHGS-A/DHFR (FIG. 12)

Ten μg of the plasmid pHGS-2/DHFR-E were digested to completion with ten units each of the restriction endonucleases EcoRI and SacI, and a fragment of approximately 275 bp was isolated from 8% acrylamide gel. Two hundred μg of the 275 bp EcoRI-SacI fragment were ligated with 50 pmol each of the synthetic fragments 5'-TATAAATA-3' and 5'-AATTTATT-TATA-3' in ligase buffer containing 50 mM NaCl using one unit of T4 DNA ligase. After ligation for 2 hours at 14° C., the DNA was digested to completion with one unit of the restriction endonuclease SacI, and a fragment of 283 bp containing the above-mentioned synthetic sequences was isolated.

Two μg of the plasmid pHGS-2Δ15 were digested to completion with four units of the restriction endonuclease BamHI, the 5' overhangs were filled in with the large fragment of the E. coli DNA polymerase I (Klenow fragment) and the enzyme was inactivated through incubation at 65° C., for 10 minutes. Subsequently the DNA was digested to completion with one unit of ClaI, and a fragment of 152 bp was isolated from an 8% acrylamide gel.

Two μg of the plasmid pHGS-2/DHFR were digested to completion with 2 units each of the restriction endonuclease enzymes ClaI and SacI, and the vector of approximately 4.6 kb was isolated from LM agarose. One hundred μg of the EcoRI-SacI fragment containing the indicated synthetic fragments and one hundred μg of the ClaI-BamHI fragment containing part of the 11 KDa transcriptional regulatory sequence were ligated with 20 μg of the ClaI-SacI digested vector pHGS-2/DHFR using one unit of T4 DNA ligase, and the DNA was transformed into HB101. Sixteen transformants that were resistant to ampicillin were selected, and cultures were grown in LB-medium containing 100 μg/ml ampicillin. DNA from these cultures was isolated and analyzed for size and for the presence of sites for the restriction endonucleases EcoRI and SacI. One plasmid displaying the expected patterns after electrophoresis in acrylamide gels was sequenced. The plasmid was designated pHGS-A/DHFR and contained the sequence:

No. 3: 5' - CTAGA AGCGA TGCTA CGCTA GTCAC

AATCA CCACT TTCAT ATTTA GAATA TATGT ATGTA

AAAAT ATAGT AGAAT TTCAT TTTGT TTTTT AAAGG

ATCTA TAAAT AAAT 3'

Figure 13:
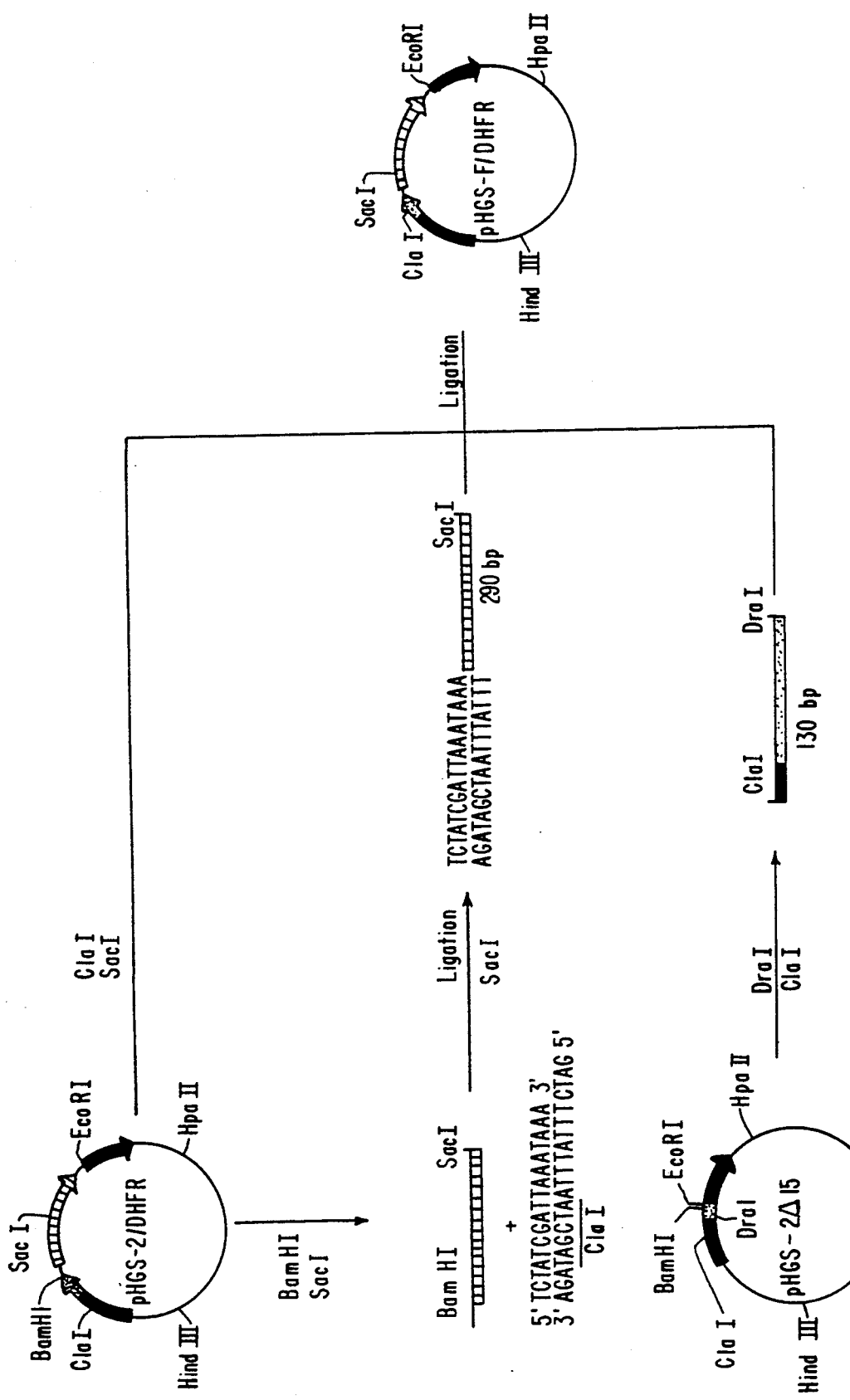
FIG. 13 represents a schematic outline of the construction of plasmid pHGS-F/DHFR.

D. Construction of Plasmid pHGS-F/DHFR (FIG. 13)

Ten μg of the plasmid pHGS-2/DHFR were digested to completion with 10 units each of the restriction endonucleases BamHI and SacI, and a fragment of 268 bp was isolated from an 8% acrylamide gel. Two hundred μg of the BamHI-SacI fragment were ligated with 50 pmol each of the synthetic fragments 5'-TCTATCGATTAAATAAA-3' and 5'-GATCTT-TATTTAATCGATAGA-3' in ligase buffer containing 50 mM NaCl final concentration, using one unit of T4 DNA ligase. After ligation for 2 hours at 14° C. the DNA was digested with one unit of the restriction endonuclease SacI, and the fragment of 290 bp containing the above-mentioned sequence was isolated. Ten μg of the plasmid pHGS-2Δ15 were digested to completion with 10 units each of the restriction endonucleases ClaI and DraI and a fragment of 130 bp was isolated from an 8% acrylamide gel.

One hundred μg each of the BamHI-SacI fragment containing the indicated synthetic fragments and the ClaI-DraI fragment containing part of the 11 KDa transcriptional regulatory sequence were ligated with 50 μg of the ClaI-SacI digested vector pHGS-2/DHFR using one unit of T4 DNA ligase, and the DNA was transformed into HB101. Sixteen transformants that were resistant to ampicillin were selected, and cultures were grown in LB-medium containing 100 μg/ml ampicillin. DNA from these cultures was isolated and analyzed for size and for the presence of sites for the restriction endonucleases SacI and ClaI. One plasmid displaying the expected patterns after electrophoresis in acrylamide gels was sequenced. The plasmid was designated pHGS-F/DHFR and contained the sequence:

No. 4: 5' - CTAGA AGCGA TGCTA CGCTA GTCAC

AATCA CCACT TTCAT ATTTA GAATA TATGT ATGTA

AAAAT ATAGT AGAAT TTCAT TTTGT TTTTT TCTAT

CGATT AAATA AAG 3'

E. Construction of Recombinant Virus RVV-6, RVV-7 and RVV-8

The recombinant viruses RVV-6, RVV-7 or RVV-8 were constructed as described before using the plasmids pHGS-2/DHFR, pHGS-A/DHFR and pHGS-F/DHFR, respectively. In each case one virus was selected for the presence of the chimeric gene consisting of the mutated 11 kDa transcriptional regulatory sequence (No. 1, 3 or 4) and the DHFR gene inserted into the VV TK-gene by blot-hybridization (Mackett et al., supra).

F. Preparation of Nuclease S1 Probes

10 μg of each of the plasmids pHGS-2/DHFR, pHGS-A/DHFR and pHGS-F/DHFR were digested to completion with 10 units of the restriction endonuclease AccI, the free-ends were dephosphorylated using one unit of BAP and the enzyme was removed through subsequent extractions with phenol, phenol-chloroform (1:1, v/v) and chloroform. The DNA's were precipitated and the free-ends were phosphorylated using polynucleotide kinase in the presence of a 2-fold molar excess of $^{32}$P-γ-ATP. The enzyme was inactivated at 65° C. for 10 minutes and the DNA's were digested to completion with 5 units of the restriction endonuclease HindIII. Fragments of approximately 1200 bp were isolated from LM agarose representing the S1 probes asymmetrically labeled at the AccI restriction endonuclease site.

G. 5' S1 Mapping of the RNA Transcripts

Monolayers of RK-13 cells were infected with 5 pfu per cell of the recombinant viruses RVV-6, RVV-7 or RVV-8. Early RNA was prepared 6 hours after infection of the cells incubated in medium containing 100

µg/ml cycloheximide (Sigma). Late RNA's were isolated from the virus infected cells 8 and 24 hours post-infection. S1 mapping was performed as described in Example 1, Section G, using the labelled S1 probes for the DHFR transcripts prepared as described in Section F.

Figure 14:
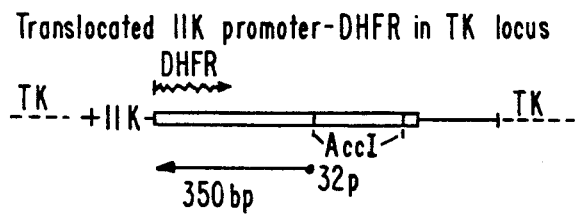
FIG. 14 The upper part represents an outline of the mapping of RNA transcripts ( ⌇⌇⌇→ ) with nuclease S1. The length of the expected band is indicated (350 bp). The lower part is the autoradiographic exposure of the nuclease S1 mapping of RNA transcripts from cells infected with RVV-6 (pHGS-2/DHFR), RVV-7 (pHGS-A/DHFR) and RVV-8 (pHGS-F/DHFR). Early RNA was extracted 6 hours after infection of cells with the different viruses incubated in the presence of 100 μg/ml cycloheximide (lanes indicated with +). Late RNA was extracted 8 and 24 hours post infection (lanes indicated with 8 or 24). The lane marked "M" consists of $^{32}$P-labelled HpaII fragments of pBR-322 giving the length position (in bp) as indicated. The positions of the S1 protected bands corresponding to RNA transcripts starting at the translocated (mutated) 11 kDa regulatory sequences are indicated.
Figure 14:
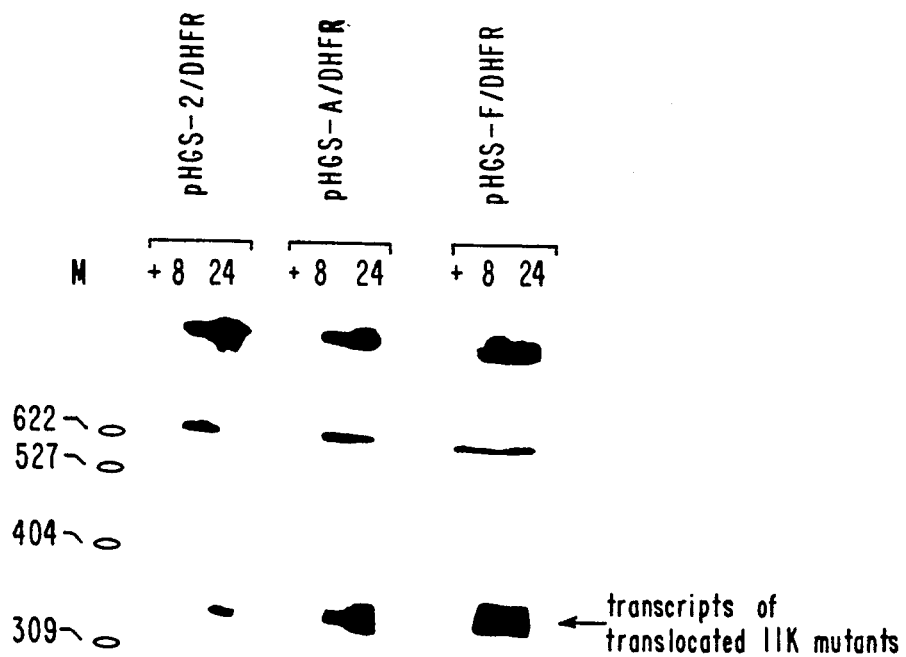

The results of the autoradiographic exposure are shown in FIG. 14. DHFR transcripts were not detectable in RNA prepared from infected cells incubated in the presence of cycloheximide, indicating that the 11 KDa regulatory sequences Nos. 1, 3 and 4 were not active early in transcription (FIG. 14, lanes indicated with +).

DHFR transcripts (indicated by arrow) were detectable 8 and 24 hours after infection in cells infected with the viruses RVV-6, RVV-7 or RVV-8 (FIG. 14, lanes indicated with 8 or 24). The amounts of DHFR transcripts derived from the mutated 11 KDa regulatory sequences Nos. 3 and 4 present in the insertion vectors pHGS-A/DHFR or pHGS-F/DHFR were at least 3- to 4-fold increased compared to the DHFR transcripts derived from the 11 KDa regulatory sequence No. 1 present in the insertion vector pHGS-2/DHFR.

What is claimed is:

1. A transcriptional regulatory sequence capable of functioning as a poxvirus late promoter selected from the group consisting of:

(a) the sequence:

```
5'    CTAGA AGCGA TGCTA
      CGCTA GTCAC AATCA CCACT
      TTCAT ATTTA GAATA TATGT
      ATGTA AAAAT ATAGT AGAAT
      TTCAT TTTGT TTTTT TCTAT
      GCTAT AAAT  3';
```

(b) the sequence:

```
5'    CTAGA AGCGA TGCTA
      CGCTA GTCAC AATCA CCACT
      TTCAT ATTTA GAATA TATGT
      ATGTA AAAAT ATAGT AGAAT
      TTCAT TTTGT TTTTT AAAGG
      ATCTA TAAAT AAAT  3';
``` and (c) the sequence:

```
5'    CTAGA AGCGA TGCTA
      CGCTA GTCAC AATCA CCACT
      TTCAT ATTTA GAATA TATGT
      ATGTA AAAAT ATAGT AGAAT
      TTCAT TTTGT TTTTT TCTAT
      CGATT AAATA AAG  3'.
```

2. A transcriptional regulatory sequence as claimed in claim 1 wherein the functionally equivalent derivative is:

```
5'    CTAGA AGCGA TGCTA
      CGCTA GTCAC AATCA CCACT
      TTCAT ATTTA GAATA TATGT
      ATGTA AAAAT ATAGT AGAAT
      TTCAT TTTGT TTTTT TCTAT
      GCTAT AAAT  3'.
```

3. A transcriptional regulatory sequence as claimed in claim 1 wherein the functionally equivalent derivative is:

```
5'    CTAGA AGCGA TGCTA
      CGCTA GTCAC AATCA CCACT
      TTCAT ATTTA GAATA TATGT
      ATGTA AAAAT ATAGT AGAAT
      TTCAT TTTGT TTTTT AAAGG
      ATCTA TAAAT AAAT  3'.
```

4. A transcriptional regulatory sequence as claimed in claim 1 wherein the functionally equivalent derivative is:

```
5'    CTAGA AGCGA TGCTA
      CGCTA GTCAC AATCA CCACT
      TTCAT ATTTA GAATA TATGT
      ATGTA AAAAT ATAGT AGAAT
      TTCAT TTTGT TTTTT TCTAT
      CGATT AAATA AAG  3'.
```

5. A recombinant vector comprising:
(a) a vector origin of replication;
(b) an antibiotic resistance gene;
(c) a chimeric gene comprising a transcriptional regulatory sequence of claim 1 operatively linked to a foreign gene encoding a prokaryotic or eukaryotic polypeptide; and
(d) a DNA segment containing the vaccinia virus thymidine kinase gene flanking said chimeric gene.

6. A recombinant vector according to claim 5 wherein the poxvirus transcriptional regulatory sequence contains a translational initiation site.

7. A recombinant vector according to claim 5 wherein a translational initiation site of the chimeric gene is provided by the foreign gene encoding a prokaryotic or eukaryotic polypeptide.

8. A recombinant vector according to claim 5 which is a plasmid capable of replication in gram-negative bacteria.

9. A recombinant vector according to claim 8 which is capable of replication in an *E. coli* strain.

10. A recombinant vector according to claim 5 wherein said foreign gene encodes a malaria antigen which is a sporozoite or merozoite surface antigen of *Plasmodium falciparum*.

11. A recombinant vector according to claim 10 wherein the malaria antigen is a sporozoite and/or a merozoite surface antigen of *Plasmodium falciparum*.

12. A recombinant vector according to claim 11 wherein the malaria antigen is a 5.1 antigen.

13. A recombinant vector according to claim 5 wherein said poxvirus DNA is vaccinia virus DNA.

14. A recombinant vector according to claim 8 which is a member of the pHGS family.

15. A recombinant vector according to claim 14 which is pHGS-1.

16. A recombinant vector according to claim 14 which is pHGS-2.

17. A recombinant vector according to claim 14 which is pHGS-2/5.1.

18. A recombinant vector according to claim 14 which is pHGS-A/DHFR.

19. A recombinant vector according to claim 15 which is pHGS-F/DHFR.

20. A recombinant infectious poxvirus containing a chimeric gene comprising a transcriptional regulatory sequence of claim 1 operatively linked to a foreign gene encoding prokaryotic or eukaryotic polypeptides and capable of expressing said foreign gene when transfected into a suitable host.

21. A recombinant infectious poxvirus according to claim 20 wherein the poxvirus transcriptional regulatory sequence contains a translational initiation site.

22. A recombinant infectious poxvirus according to claim 20 wherein the translational inition site of the chimeric gene is provided by the foreign gene encoding a prokaryotic or eukaryotic polypeptide.

23. A recombinant infectious poxvirus according to claim 20 wherein said foreign gene encodes a malaria antigen which is a sporozoite or merozoite surface antigen of *Plasmodium falciparum.*

24. A recombinant infectious poxvirus according to claim 23 wherein the malaria antigen is a sporozoite and/or merozoite surface antigen of *Plasmodium falciparum.*

25. A recombinant infectious poxvirus according to claim 24 wherein the malaria antigen is a 5.1 antigen.

26. A recombinant infectious poxvirus according to claim 20 which is an infectious recombinant vaccinia virus.

27. An infectious vaccinia virus of claim 26 which is RVV-1.

28. An infectious vaccinia virus of claim 26 which is RVV-2.

29. An infectious vaccinia virus of claim 26 which is RVV-4.

30. An infectious vaccinia virus of claim 26 which is RVV-7.

31. An infectious vaccinia virus of claim 26 which is RVV-8.

32. A method for the manufacture of the recombinant vector of claim 5 comprising the steps of:

(a) preparing a vector containing poxvirus DNA, said DNA comprising:
  (i) a transcriptional regulatory sequence, and
  (ii) a restriction endonuclease site up or down stream of said transcriptional regulatory sequence, and
  (iii) DNA from a non-essential segment of the poxvirus genome flanking said regulatory sequence and said restriction endonuclease site; and
(b) inserting at least one foreign gene encoding a prokaryotic or eukaryotic polypeptide into said restriction endonuclease site next to said transcriptional regulatory sequence.

33. The method of claim 32 wherein said poxvirus DNA is vaccinia virus DNA.

34. A method for the manufacture of a recombinant infectious poxvirus comprising the steps of:
(a) preparing a recombinant vector according to claim 32;
(b) providing at least one cell infected with a virus from a genus of poxvirus;
(c) transfecting said cell with said recombinant vector, whereby homologous recombination occurs between the DNA of said poxvirus and said poxvirus DNA contained in said recombinant vector; and
(d) isolating from said cell a recombinant infectious poxvirus capable of expressing said foreign gene encoding prokaryotic or eukaryotic polypeptides.

35. The method according to claim 34 wherein said poxvirus DNA is vaccinia virus DNA.

36. A recombinant infectious poxvirus according to claim 20 wherein said foreign gene encodes interleukin-2.

37. A recombinant infectious poxvirus according to claim 20 wherein said foreign gene encodes an HTLV-III envelope protein.

38. A recombinant infectious poxvirus according to claim 20 wherein said foreign gene encodes growth hormone releasing factor.

* * * * *

UNITED STATES PATENT AND TRADEMARK OFFICE
CERTIFICATE OF CORRECTION

PATENT NO. : 5,017,487

DATED : May 21, 1991

INVENTOR(S) : Hendrik Gerard Stunnenberg and Riccardo Wittek

It is certified that error appears in the above-identified patent and that said Letters Patent is hereby corrected as shown below:

Title page
 Item
 [21] "Appl. No.:845,014"   should be Appl. No.: 845,104

Signed and Sealed this

Twenty-ninth Day of December, 1992

*Attest:*

DOUGLAS B. COMER

*Attesting Officer*   *Acting Commissioner of Patents and Trademarks*